(12) United States Patent
Kim et al.

(10) Patent No.: US 8,501,996 B2
(45) Date of Patent: Aug. 6, 2013

(54) IMINECALIXARENE DERIVATIVES AND AMINOCALIXARENE DERIVATIVES, METHOD OF PREPARATION THEREOF, AND SELF-ASSEMBLED MONOLAYER PREPARED BY THE METHOD, FIXING METHOD OF OLIGO-DNA BY USING THE SELF-ASSEMBLED MONOLAYER, AND OLIGO-DNA CHIP PREPARED BY THE METHOD

(75) Inventors: Tae Sun Kim, Chuncheon-Si (KR);
Keum Soo Song, Chuncheon-Si (KR);
Jung Hoon Kim, Chuncheon-Si (KR);
Hyung Sub Kim, Chuncheon-Si (KR)

(73) Assignee: Biometrix Technology Inc., Chuncheon-si (KR)

( * ) Notice: Subject to any disclaimer, the term of this patent is extended or adjusted under 35 U.S.C. 154(b) by 27 days.

(21) Appl. No.: 13/192,268

(22) Filed: Jul. 27, 2011

(65) Prior Publication Data
US 2012/0202711 A1 Aug. 9, 2012

Related U.S. Application Data

(62) Division of application No. 11/816,022, filed as application No. PCT/KR2006/001753 on May 11, 2006, now Pat. No. 8,013,188.

(30) Foreign Application Priority Data

Oct. 13, 2005 (KR) .................. 10-2005-0096322
Nov. 4, 2005 (KR) .................. 10-2005-0105340

(51) Int. Cl.
*C07C 211/00* (2006.01)
(52) U.S. Cl.
USPC ............ 564/326; 564/315; 564/321; 564/323
(58) Field of Classification Search
None
See application file for complete search history.

(56) References Cited

U.S. PATENT DOCUMENTS

| 6,033,773 | A | 3/2000 | Yang et al. | |
|---|---|---|---|---|
| 8,013,188 | B2 * | 9/2011 | Kim et al. ............. | 564/326 |
| 2003/0228974 | A1 | 12/2003 | Katz et al. | |

FOREIGN PATENT DOCUMENTS

| JP | 05-271175 | 10/1993 |
|---|---|---|
| KR | 2002-0031734 | 5/2002 |
| KR | 10-0786577 B1 | 12/2007 |
| KR | 10-0869916 B1 | 11/2008 |
| WO | WO 2007/052879 A1 | 5/2007 |

OTHER PUBLICATIONS

Dermody et al., "Synthesis, Characterization, and Chemical Sensitivity of Self-Assembled Bilayers Composed of Polydiacetylenes and Calix[4]arenes Chemically Modified on the Upper Rim", Langmuir, 15, Sep. 11, 1999, pp. 8435-8440, American Chemical Society.
Smilowitz et al., "Imaging nanometer-thick patterned self-assembled monolayers via second-harmonic generation microscopy", Journal of Applied Physics, 81(5), Mar. 1, 1997, pp. 2051-2054, American Institute of Physics.
Yang et al., "Synthesis and NLO Properties of Polar Self-Assemblies of Molecular Pyramids Covalently Bound on Oxide Surfaces", Angewandte Chemie, International Edition in English, 35, No. 5, 1996, pp. 538-540.
Yang et al., "A Molecular Architectural Approach to Second-Order Nonlinear Optical Materials", Materials Research Society Symposium Proceedings, vol. 392, 1995, pp. 27-32.
Jakobi et al. "Long-chain alkyl ethers of p-nitro and p-aminocalixarenes", New Journal of Chemistry, vol. 20, No. 4, 1996, pp. 493-501.
Gutsche et al., "Calixarenes 12, The Synthesis of Functionalized Calixarenes", Tetrahedron, vol. 42, No. 6, pp. 1633-1640, 1986, Elsevier Science Publishers, Amsterdam, NL.
Li et al., "Molecular Architecture of Calixarenes and Their Self-Assembled Mono- and Multi-layers for Nonlinear Optical (NLO) Applications", Synthetic Metals 86, 1997, pp. 1849-1850, Elsevier Science S.A.
Schmidt et al., "Modification of calyx[4]arenes with CMPO-functions at the wide rim. Synthesis, solution behavior, and separation of actinides from lanthanides", Organic & Biomolecular Chemistry, vol. 1, No. 22, 2003, pp. 4089-4096, The Royal Society of Chemistry.
The extended European search report and supplementary European search report for the European patent application No. EP 06757689.2 dated Apr. 22, 2010.
Office action for the Japanese Patent Application No. JP2008-535434 dated Jul. 4, 2011.
Andrew Solovyov et. al., Calix[4]arenes Bearing a-Amino-a-Hydroxyphosphonic Acid Fragments at the Upper Rim, Heteroatom Chemistry, pp. 58-67, vol. 12, No. 2, 2001.
Youheng Shi, et al., Interactions between aminocalixarenes and nucleotides or nucleic acids, J. Chem. Soc., Perkin Trans., pp. 1797-1803, 1999.
International Search Report for PCT/KR2006/001753 dated Sep. 28, 2006.
International Preliminary Report on Patentability dated Apr. 16, 2008 and Written Opinion dated Sep. 26, 2006 for PCT/KR2006/001753.

* cited by examiner

*Primary Examiner* — Sudhakar Katakam
(74) *Attorney, Agent, or Firm* — Arent Fox LLP

(57) ABSTRACT

The present invention relates to novel iminecalixarene derivatives, method of preparation thereof, and self-assembled monolayer prepared by the method, fixing method of oligo-DNA by using the self-assembled monolayer, and oligo-DNA chip prepared by the method. Also, the present invention relates to novel aminocalixarene derivatives, method of preparation thereof, and self-assembled monolayer prepared by the method, fixing method of oligo-DNA wherein the oligo-DNA is voluntarily fixed by molecular recognition on said self-assembled monolayer in a liquid phase, and oligo-DNA chip prepared by the method.

4 Claims, 14 Drawing Sheets

Fig. 7
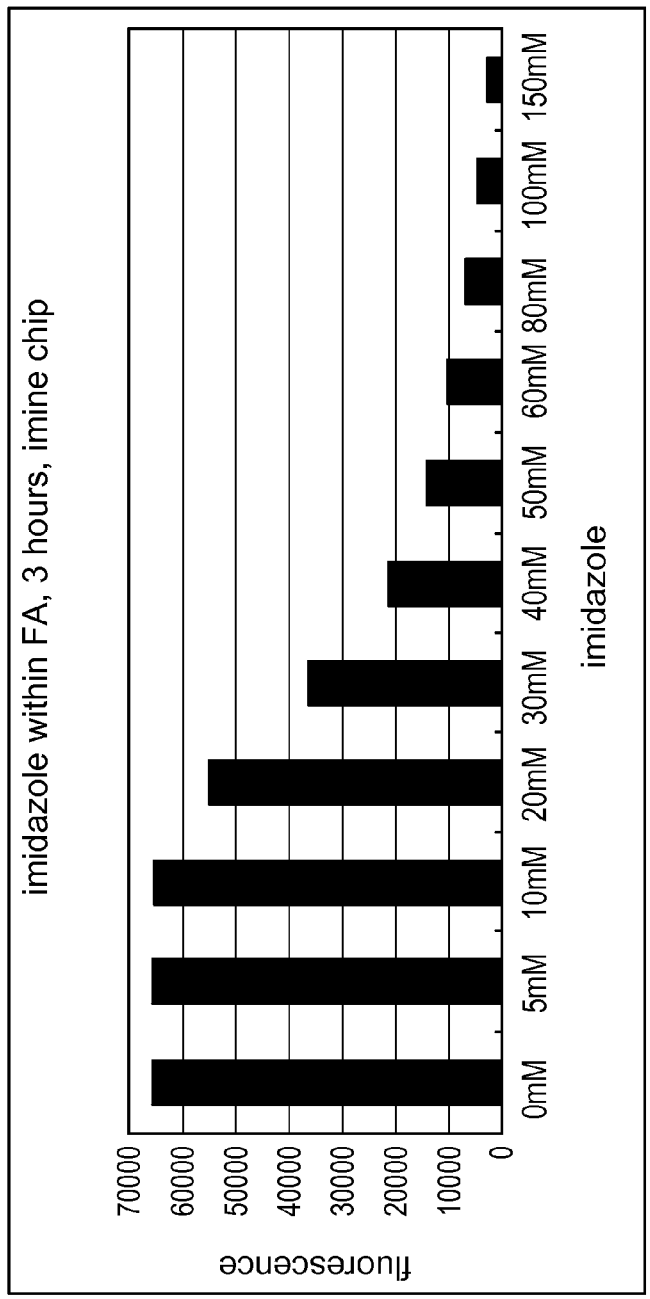
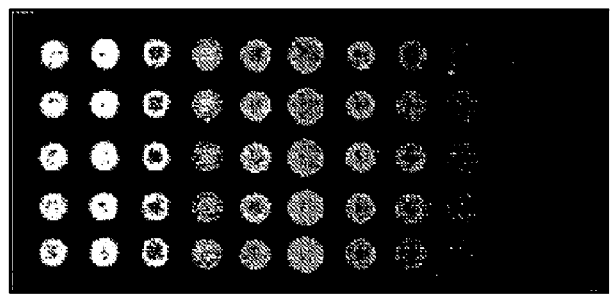
LM=90, PMT=65

Technology for preparing oligo-DNA chip by voluntary molecular recognition combined with the space securing technology Fig. 11
Calculation of the number of aminocalixarene derivative constituting a monolayer
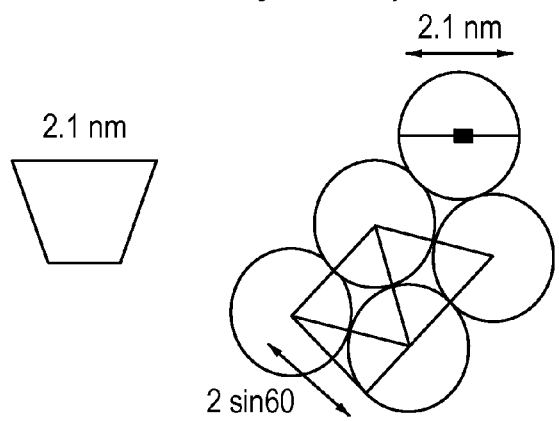
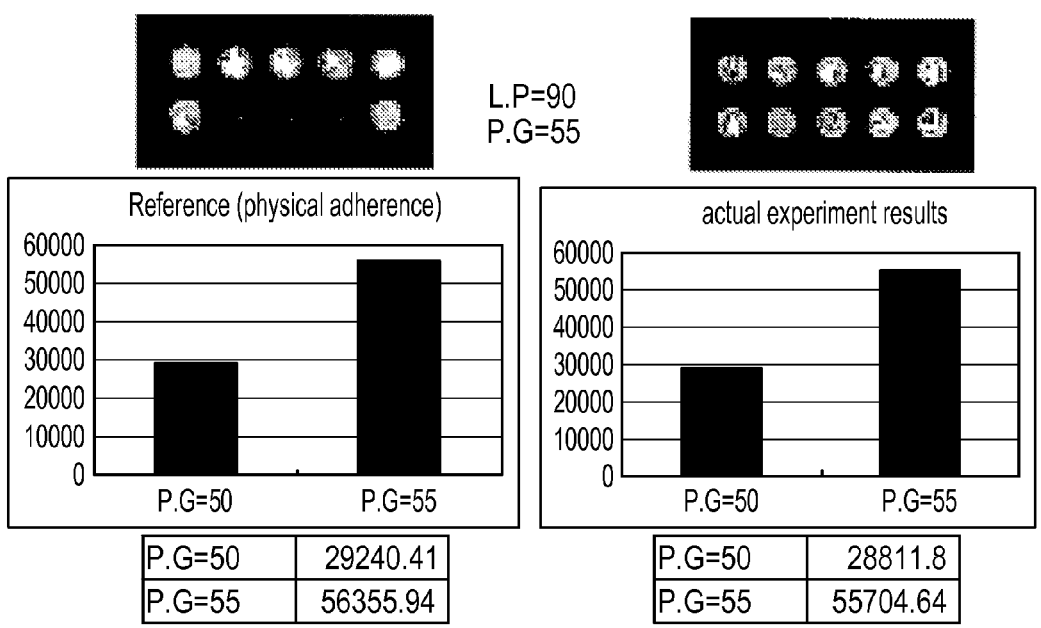
1) results from drying oligo-DNA wherein fluorescence is attached
1) results obtained after hybridization Fig. 14
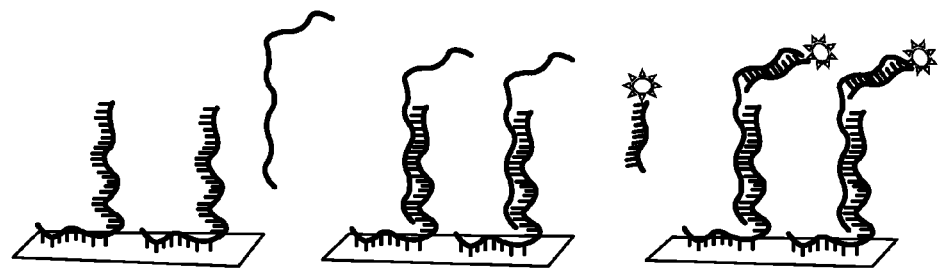
| m(T)55 | ○ ○ |
| m(C)57 | ○ ○ |
| m(A)55 | ○ ○ |
| m(G)57 | ○ ○ |
T
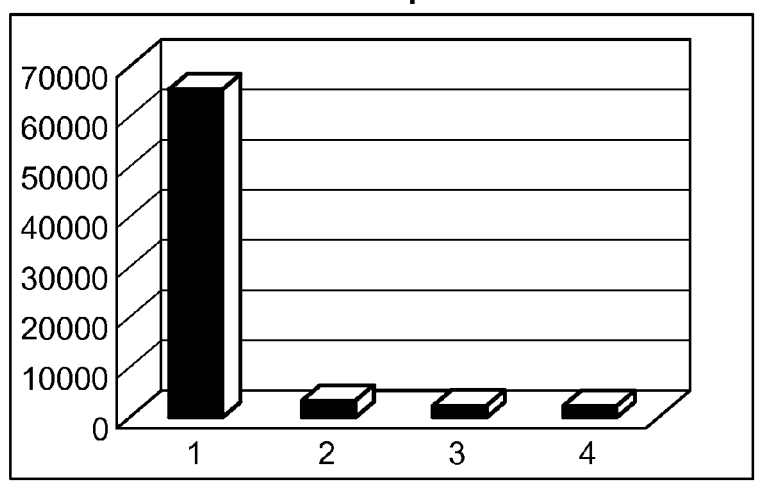
L.P = 90
P.G = 70
A
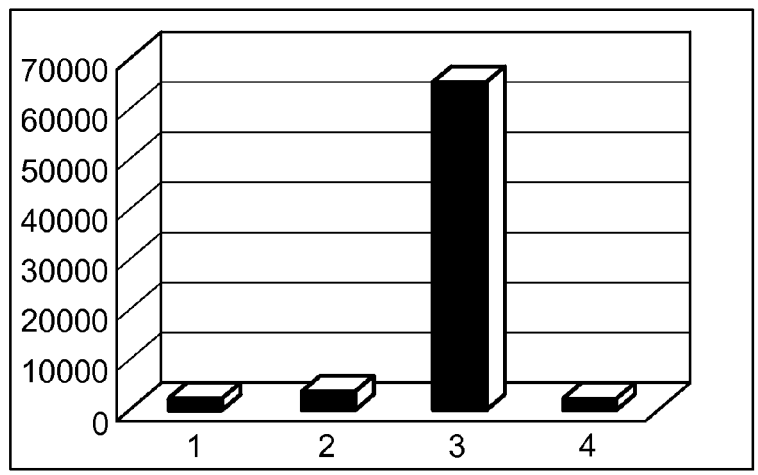
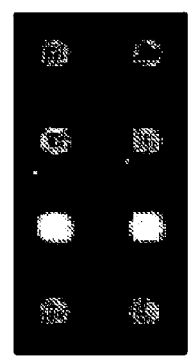
L.P = 90
P.G = 70

Fig. 16
L.P=90
P.G=65
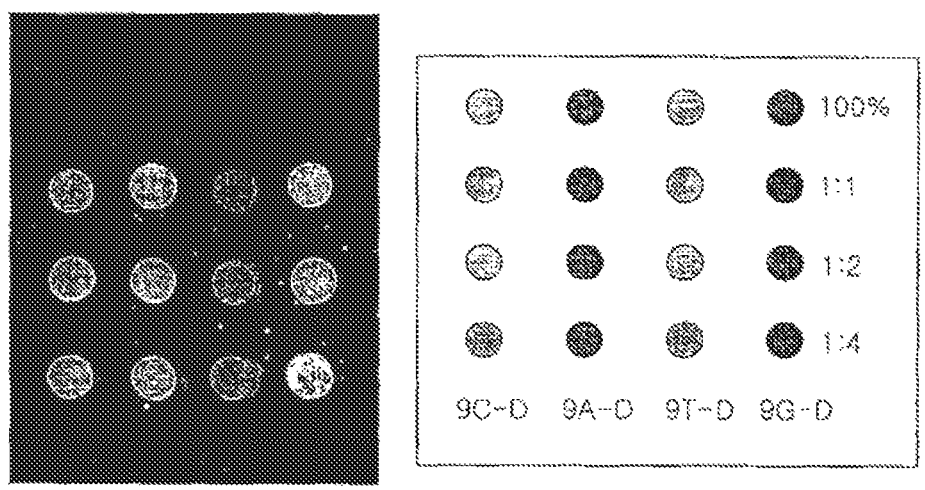
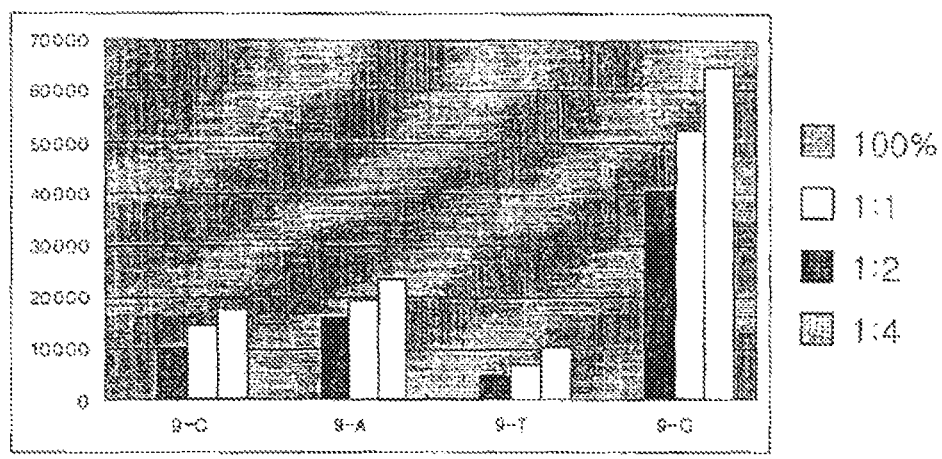
|      | 9-C      | 9-A      | 9-T      | 9-G      |
|------|----------|----------|----------|----------|
| 100% | 1.083005 | 1.87881  | 3.157046 | 16.57297 |
| 1:1  | 10191.47 | 15913.01 | 4702.93  | 40460.59 |
| 1:2  | 14496.31 | 19368.8  | 7032.801 | 52159.34 |
| 1:4  | 17438.67 | 23266.55 | 10169.03 | 64578.48 |

IMINECALIXARENE DERIVATIVES AND AMINOCALIXARENE DERIVATIVES, METHOD OF PREPARATION THEREOF, AND SELF-ASSEMBLED MONOLAYER PREPARED BY THE METHOD, FIXING METHOD OF OLIGO-DNA BY USING THE SELF-ASSEMBLED MONOLAYER, AND OLIGO-DNA CHIP PREPARED BY THE METHOD

This application is a divisional of application Ser. No. 11/816,022, filed Nov. 28, 2007, now U.S. Pat. No. 8,013,188 which is a National Stage of International Application PCT/KR2006/001753, filed May 11, 2006, published Apr. 19, 2007, under PCT Article 21(2) in English; which claims the priority of KR 10-2005-0105340, filed Nov. 4, 2005, and KR 10-2005-0096322, filed Oct. 13, 2005. These prior applications are hereby incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Mar. 20, 2012, is named 33397002.txt and is 8,458 bytes in size.

TECHNICAL FIELD

The present invention relates to novel iminecalixarene derivatives, method of preparation thereof, and self-assembled monolayer prepared by the method, fixing method of oligo-DNA by using the self-assembled monolayer, and oligo-DNA chip prepared by the method.

More particularly, the present invention relates to a method for preparing an iminecalixarene compound capable of fixing an oligo-DNA having consecutive guanine bases on the surface of a solid substrate by molecular recognition in a monolayer on a glass substrate or gold substrate and a method for preparing an oligo-DNA monolayer, i.e., an oligo-DNA chip using a self-assembled monolayer thereof.

Also, the present invention relates to novel aminocalixarene derivatives, method of preparation thereof, and self-assembled monolayer prepared by the method, fixing method of oligo-DNA by irreversible, voluntary molecular recognition of the oligo-DNA in said self-assembled monolayer, and oligo-DNA chip prepared by the method.

More particularly, the present invention relates to an aminocalixarene derivative fixing an oligo-DNA having consecutive guanine bases on the surface of a solid substrate by irreversible/voluntary molecular recognition of multiple bases, a technology preparing it as a monolayer biochip substrate on a solid substrate such as glass or gold substrate, etc. and a method for preparing an oligo-DNA chip fixing an oligo-DNA on a biochip substrate prepared by said preparation technology in high density as a monolayer.

BACKGROUND ART

After the National Human Genome Research Institute and Celera Genomics have competitively researched and studied human genome under the Human Genome Project, the information map of human gene was completed in 2000, which put spurs to the development of a diagnostic oligo-DNA chip using studies on DNA functions, variant DNA search, and the information thereon. In particular, the oligo-DNA chip for searching a single nucleotide polymorphism (SNP) is expected to be used for diagnosing genetic diseases caused by defective DNA, or cancer at an early stage, etc. Further, it has been a world-wide trend to research and study the technology for manufacturing an oligo-DNA chip wherein a number f oligo-DNAs are fixed on a substrate, the oligo-DNA chip providing information on accurate virus infection routes based on the virus typing, analysis on its harmfulness or harmlessness, etc., and the prediction of occurrence of a cancer, etc. based on the typing of a group of carcinogenic viruses. In fact, an oligo-DNA chip that can type the human papiloma virus (HPV) has been officially approved by the Korea Food & Drug Administration (KFDA) in Korea for the first time in the world as a diagnostic and preventive medical biochip for predicting the probability of the occurrence of cervical cancer. Further, the oligo-DNA chip for diagnosing the cervical cancer has already been officially approved by KFDA, and it is now in use.

An oligo-DNA chip comprises short DNAs (oligo-DNAs) being 15-50mer fixed on a substrate. Thus, whereas the c-DNA chip, which has been used for analyzing DNA variants, conventionally utilized a simple physical absorption method, the oligo-DNA chip still utilizes the method that was developed several decades ago, such as a fixing method based on the use of the imine bonding method by a chemical bonding between aldehyde and amine; or a fixing method based on the amine bonding method following a reduction reaction to increase the bonding after the chemical bonding between aldehyde and amine functional group. It is because it has not yet been successful to develop a bio-chip substrate that is superior to the aldehyde-chip in terms of reproducibility and convenience. However, in the aldehyde-chip substrate, the amine functional group attached to the terminal of the oligo-DNA by means of a synthesis technology is chemically bonded by an imine bonding onto the aldehyde-chip; thus, there is a huge difference in the theoretical maximum density between the amount of the fixed DNA and the amount of the fixed oligo-DNA that is combinable with c-DNA in an actual hybridization reaction. Further, the density of the fixed oligo-DNA constantly changes because it is heavily influenced by the fixation conditions, and thus the development of a chip with reproducibility has not been successful.

A technology applying the bonding method of streptavidin-biotin is also widely used, and said technology is a method for producing oligo-DNAs by fixing streptavidin-biotin onto the surface of a solid substrate by means of a physical absorption, chemical bonding, etc., and then by making streptavidin-biotin molecularly recognize the biotin functional group of the oligo-DNA to which the biotin is attached (Science, 1993; Vol. 262, pp 1706-1708). However, the technology applying the chemical bonding method or the bonding method of streptavidin-biotin, etc. is still behind the aldehyde-chip substrata in performance.

Meanwhile, in a protein chip, the active position of an antibody exists at one place of the protein fixed on the surface, and thus there would be no problem in obtaining results if only said place is located where it can bond with an antigen. However, in an oligo-DNA chip, at least a certain number of bases of most of the oligo-DNAs must bond with the approaching c-DNAs in a hybridization reaction, and thus the number of the bases that bond must be maximized by getting the c-DNAs as close to the floor on which oligo-DNAs are fixed as possible. To this end, an opinion has been suggested since European society of 2003 that between the fixed oligo-DNAs, there should be maintained some room to allow the c-DNAs free access, and now, a study of the technology for securing such room has become a hot subject in the art.

Oligo-DNAs that are fixed on the surface at molecular level tend to voluntarily assemble together, and thus it is relatively difficult to apply the technology to the chemically bonded oligo-DNA chip. Accordingly, an oligo-DNA, 20-25-mer of which would otherwise be enough, is lengthened up to 50-mer so that the approaching c-DNA may not have to come down to the bottom, and the number of bases that bond during the hybridization reaction is increased to reproduce the result of a diagnosis. However, it takes from at least several hours to more than a day for the result to become clearly readable, and thus the technology is not distinguished from the conventional diagnostic technology concerning an analysis of Bird flue virus, etc.

DISCLOSURE OF INVENTION

Technical Problem

Problems found with the conventional methods for fixing oligo-DNAs, such as chemical bonding method and streptavidin-biotin method, etc. are as follows:

1. Homogeneousness of the fixation density: the chemical bonding method is the most widely used one, and it is known that while oligo-DNAs are fixated, a chemical reaction occurs between the aldehyde functional group (—CHO) and the amine functional group (—$NH_2$), thus fixing the oligo-DNAs chemically; during the reaction, one $H_2O$ falls out therefrom to have the oligo-DNA fixed in the form of an imine bonding (—C=N—). However, since this reaction takes place in an aqueous solution phase, the fixation density is not homogeneous, i.e., is not replicated. In addition, the density of the oligo-DNA is difficult to be maintained homogeneously, since the reverse reaction occurs easily wherein the imine bonding comes back to the original functional group in an aqueous solution phase. Further, to minimize such a reverse reaction, a reduction reaction for the imine bonding can be rendered by using a reduction agent such as $NaBH_4$, etc., but such a reduction reaction influences the bonding of oligo-DNAs, which then results in failing to constantly maintain the length of the fixed oligo-DNAs. Due to such different result from each production, the development of a novel oligo-DNA chip tends to be prolonged, which is regarded as a huge obstacle to the manufacture of the oligo-DNA chip. At the same time, the fixed oligo-DNA is used for a diagnosis by bonding with c-DNAs to which a fluorescent material (e.g., Cy-3) is attached in proportion to the density of said oligo-DNA, and then informing the existence of c-DNAs and its concentration. Thus, if the density of the oligo-DNA is not constantly maintained, the oligo-DNA cannot be manufactured as a commercial product, and to this reason, many companies that have invested a fortune still fail to get their intended results.

2. Necessity for securing room between oligo-DNAs for the c-DNAs access (a ultra-high speed hybridization reaction is impossible): c-DNAs, wherein the template gene of a pathogen is amplified through a polymerase chain reaction (PCR), must eventually be attached to an oligo-DNA chip. However, as shown in FIG. 7, if the distance between the fixed DNAs is too close, c-DNAs cannot easily approach the lower part of the oligo-DNAs. Currently, there are many oligo-DNA chips which require from several hours to over one day for a hybridization reaction, and this is mainly because there is not enough room to allow the approaching c-DNAs an easy access to the base at the bottom portion of the fixed oligo-DNAs to bond therewith. Accordingly, a technology to secure a room at a proper level between oligo-DNAs is necessary, but people have not come up with a good solution yet. To solve this problem, it is necessary to develop a technology that secure room at a proper level to allow c-DNAs easy access to the DNA chip substrate by using the surface bonding of consecutive bases.

3. Attachment of functional groups: the technology of fixing an oligo-DNA by using a chemical bonding or the bonding of streptavidine-biotin is possible only by attaching a biotin or an amine functional group to the oligo-DNA. However, the cost for attaching such functional group after the synthesis of an oligo-DNA is three to ten times greater than the conventional way of the synthesis of the oligo-DNA wherein few functional groups are attached. Moreover, even when only tens of oligo-DNAs are fixed to produce oligo-DNA chips for marketing, hundreds or thousands of samples of oligo-DNAs must be tested, and the cost required therefor, not to mention the cost for manufacturing a finished product, could be hundreds or millions of dollars, which is another obstacle for the development of the oligo-DNA chip. To minimize such problem, it is necessary to develop a technology for manufacturing an oligo-DNA chip by using oligo-DNAs without a functional group attached thereto.

4. A chemical bonding between an amine functional group attached to the three bases of A, C and G, and a functional group of the aldehyde-chip substrate: the aldehyde-chip substrate produces an oligo-DNA chip where the oligo-DNAs are fixed by reacting with the aldehyde functional group on the surface the oligo-DNAs to which an amine functional group is attached. However, the amine functional group is already attached to said three bases which constitute three quarters of the numerous bases that are attached to the oligo-DNA, and the oligo-DNAs at the middle part are fixed much faster than the bases are fixed when an amine functional group attached to the terminal of the oligo-DNA reacts with aldehyde, and thus the number of bases available for a multiple-hydrogen bonding with the approaching, fluorescently attached c-DNAs is not sufficient. Aldehyde also can be hydrogen-bonded with the base of the c-DNA that additionally approaches, and thus to remove it, a chemical treatment should follow after oligo-DNAs are fixed, and here, it is known that the replication of the produced DNA chip becomes more problematic.

5. A technology of diagnosing SNP: it is the biggest advantage of the oligo-DNA chip among technologies for analyzing DNAs to type various kinds of DNA present in numerous viruses such as bird flue, swine plague, cancer-spreading viruses, etc. However, such viruses are mostly those in novel forms generated through variation of their original kinds of viruses, and as such, in many cases, there are not much difference in base sequence between the original kind of the virus and its variant. In particular, it is problematic that there are many virus groups that show differences only in one or two base sequences. Accordingly, the most important part in developing the oligo-DNA chip is producing an oligo-DNA chip that is able to identify a variant of a single base at the on-off level, i.e., to diagnose SNP. Many researchers agree that the oligo-DNA chip, which is manufactured by using the aldehyde-chip substrate that is currently used the most, has no sufficient room between the fixed oligo-DNAs necessary to identify such variants of single base, and thus that it is impossible to produce a diagnostic oligo-DNA chip for identifying variants of single base.

6. Technology of manufacturing low price chips: if functional groups such as amine, biotin, etc. are attached to fix an oligo DHA, the cost of the oligo-DNA goes up more than ten times, and the chip must be covered with DNAs at high concentration for hindering bases from bonding on the surface. Then the cost for manufacturing such oligo-DNA chip goes enormously high.

Technical Solution

The object of the present invention is to provide iminecalix derivatives being capable of molecular recognition of an oligo-DNA having consecutive guanine groups, and the method for preparing them, in order to solve the problems of the above-mentioned conventional oligo-DNA fixation method, such as homogeneousness of the fixation density, securing sufficient room between oligo-DNAs, attachment of functional groups, etc.

Another object of the present invention is to provide a monolayer of oligo-DNA wherein, by attaching said iminecalixarene derivatives to a glass substrate (an amine slide glass) or to a golden substrate (golden thin layer or gold), all kinds of oligo-DNAs are densely packed and maintain room at a proper level without having any treatment; that is, to provide a monolayer of iminecalixarene derivatives that are capable of making oligo-DNA chips.

More specifically, the object of the present invention is to provide a monolayer of oligo-DNAs wherein oligo-DNAs having at least seven consecutive guanines are densely packed and maintain a room at a proper level without having any treatment, that is, to provide a monolayer of iminecalixarene derivatives that can make an oligo-DNA chip.

As another aspect of the present invention, the object of the present invention is to provide an oligo-DNA chip which can solve all the conventional oligo-DNA chip's problems of not being able to have a ultra-high speed hybridization reaction, of not being able to secure the technology to diagnose SNP, of the chemical bonding of the amine functional group attached to the three bases of A, C and G with the functional group of the aldehyde-chip substrate, of difficulty in homogeneous density in fixing oligo-DNAs on a chip, etc., at once. That is, the object of the present invention is to provide aminocalixarene derivatives capable of irreversible molecular recognition of consecutive guanine group, a method for manufacturing a substrate of oligo-DNA chip made in the form of a self-assembled monolayer thereof, and an oligo-DNA chip manufactured through irreversible fixation of oligo-DNAs by the voluntary molecular recognition on the surface of the chip substrate.

Another object of the present invention is to provide a monolayer of oligo-DNAs wherein, by attaching the above-mentioned compound to a solid substrate such as a glass substrate (amine slide glass), etc. having an amine functional group, or to a golden substrate (golden thin layer or gold) as a monolayer, all kinds of oligo-DNAs are fixed with the maximum density without any treatment and maintain room at a proper level, that is, to provide a chip substrate manufactured by using aminocalixarene derivatives capable of producing an oligo-DNA chip.

Another object of the present invention is to provide an oligo-DNA monolayer, wherein the consecutive guanine bases are fixed onto the surface in a line, so that the oligo-DNAs are fixed with the maximum density without any treatment and maintain room at a proper level, that is to provide a technology for manufacturing an oligo-DNA chip.

BRIEF DESCRIPTION OF THE DRAWINGS

FIG. 7 shows the results of competitive reaction using imidazole functional group having a similar structure in order to verify that the guanine base is selectively recognized by molecular recognition when fixing oligo-DNA to the iminecalixarene derivative self-assembled monolayer of the present invention.

FIGS. 10 & 11 are schematic diagrams of the fixing method of oligo-DNA having consecutive guanine bases by voluntary molecular recognition of the present invention and the actual experimental results of fixation of the maximum density.

FIGS. 14 & 15 are actual experimental results showing that SNP differentiation is possible to an on-off level using high speed hybridization.

FIG. 16 is a result of actual competitive reaction showing that guanine base selectively performs high speed fixation than other bases in fixation.

MODE FOR THE INVENTION

Figure 1:
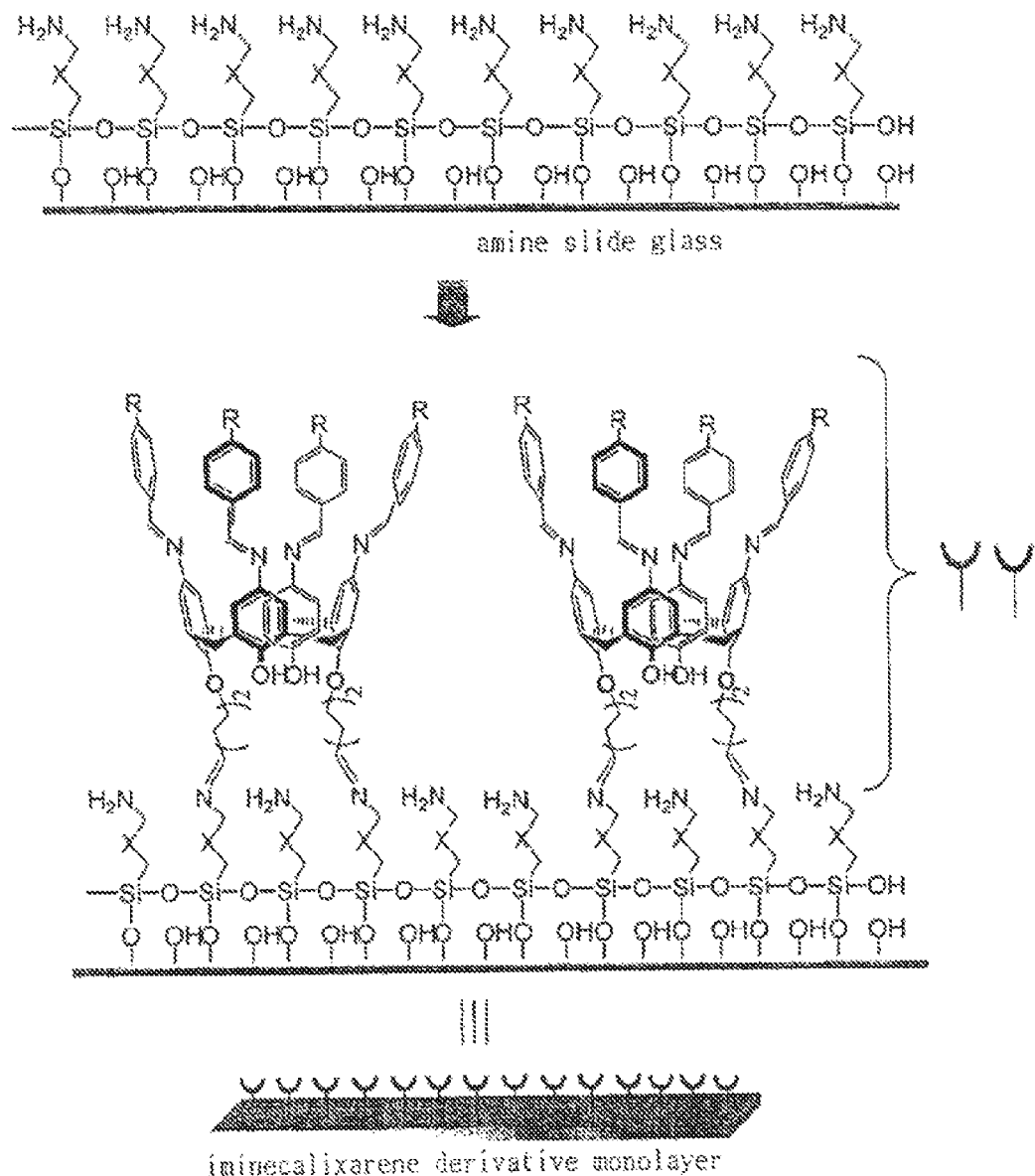
FIG. 1 is a schematic diagram of the preparation process of the self-assembled monolayer on the glass substrate (amine slide glass) of the iminecalixarene derivative of the present invention.

The novel iminecalixarene derivative of the present invention has a structure of the following formula 1 or 2. Said iminecalixarene derivative is a compound essential to the self-assembled monolayer used in the fixing method of an oligo-DNA having at least 7 consecutive guanine groups.

[Formula 1]

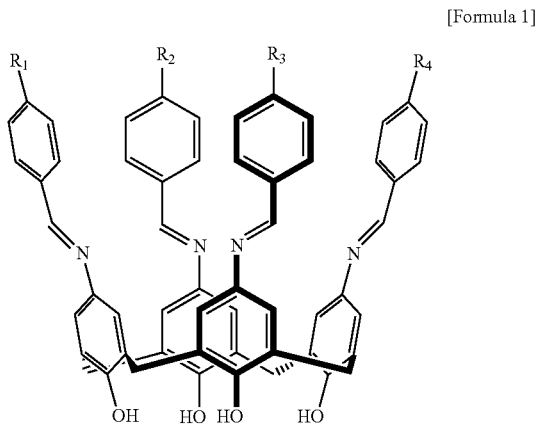

(wherein, R$_1$, R$_2$, R$_3$ and R$_4$ are independently selected from the group consisting of —H, —CH$_3$, —C$_2$H$_5$, —C$_3$H$_7$, —OCH$_3$, —Cl, —C$_6$H$_5$ and —COOR, and in said —COOR, R represents —CH$_3$ or —C$_2$H$_5$.)

[Formula 2]

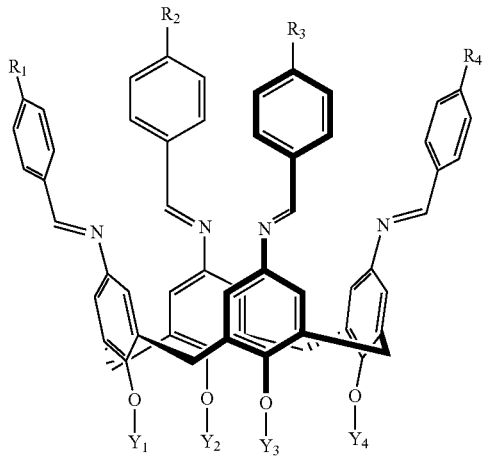

(wherein, R$_1$, R$_2$, R$_3$ and R$_4$ are independently selected from the group consisting of —H, —CH$_3$, —C$_2$H$_5$, —C$_3$H$_7$, —OCH$_3$, —Cl, —C$_6$H$_5$ and —COOR, and in said —COOR, R represents —CH$_3$ or —C$_2$H$_5$; also, said Y$_1$, Y$_2$, Y$_3$ and Y$_4$ are independently selected from the group consisting of —H, —(CH$_2$)$_n$—CH=O, —(CH$_2$)$_n$—SH, —(CH$_2$CH$_2$O)$_m$—CH$_2$CH$_2$—CH=O, —(CH$_2$CH$_2$O)$_m$—CH$_2$CH$_2$—SH, —(CH$_2$)$_m$—C$_6$H$_4$—(CH$_2$)$_c$—Z and —CO—(CH$_2$)$_{m-1}$—C$_6$H$_4$—(CH$_2$)$_c$—Z (wherein, n=2~15, m=1~10, c=0~10, Z=—SH, —CHO, —COOH or —NH$_2$).)

The present invention also provides a method for preparing an iminecalixarene derivative compound of said formulae 1 and 2.

The 5,11,17,23-tetraminocalix[4]arene compound of the following formula 3 is synthesized by a reduction reaction after calix[4]arene is transformed to 5,11,17,23-tetranitrocalix[4]arene according to the method of the following cited reference 1 [Cited Reference 1: Journal of Organic Chemistry, 1990, Vol 55, pp 5639-5643; Journal of Organic Chemistry, 1979, Vol 44, pp 1233-1238].

[Formula 3]

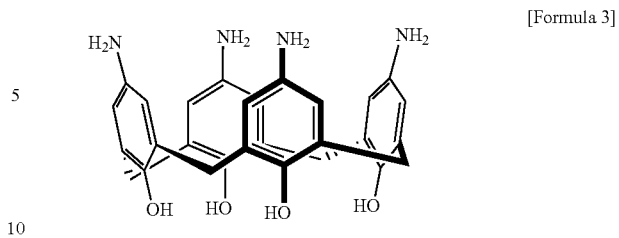

The iminecalixarene derivative compounds of said formula 1 of the present invention is synthesized by reacting the amine functional group of formula 3 with the aromatic aldehyde of the following formula 4, with the 5,11,17,23-tetraminocalix[4]arene compound of said formula 3 as a starting material (see reaction 2 of the following example).

[Formula 4]

(wherein, R is selected from the group consisting of —H, —CH$_3$, —C$_2$H$_5$, —C$_3$H$_7$, —OCH$_3$, —Cl, —C$_6$H$_5$ and COOR', and in said COOR', R' represents —CH$_3$ or —C$_2$H$_5$.)

Also, the iminecalixarene derivative compound of formula 2 of the present invention is synthesized by reacting the compound of formula 1 with an aldehyde compound wherein a halogen is attached at the terminal group, so that it has a terminal group wherein an aldehyde or thiol is attached at the first and third —OH group position of formula 1 (see reactions 3~5 of the following example).

Said halogenated aldehyde is selected from the group consisting of X—(CH$_2$)$_n$—CH=O, X—(CH$_2$)$_n$—SH, X—(CH$_2$CH$_2$O)$_m$—CH$_2$CH$_2$—CH=O, X—(CH$_2$CH$_2$O)$_m$—CH$_2$CH$_2$—SH, X—(CH$_2$)$_m$—C$_6$H$_4$—(CH$_2$)c-Z and X—CO—(CH$_2$)$_{m-1}$—C$_6$H$_4$—(CH$_2$)$_c$—Z, wherein n=2~15, m=1~10, c=0~10, X=—Cl, —Br, —I or —OSO$_2$C$_6$H$_4$CH$_3$, Z=—SH, —CHO, —COOH or —NH$_2$.

In addition, the present invention provides a self-assembled monolayer solid substrate prepared by attaching to a gold substrate, an iminecalixarene derivative with a thiol group attached.

In addition, the present invention provides a self-assembled monolayer solid substrate prepared by attaching an iminecalixarene derivative to a solid substrate such as glass, silicon wafer or crystal, etc. through an imine bonding, and a self-assembled monolayer solid substrate prepared by attaching an iminecalixarene derivative to a solid substrate such as glass, silicon wafer or crystal, etc. through a chemical bonding such as ester, ether and amide bonding, etc.

In addition, the present invention provides an oligo-DNA monolayer wherein all kinds of oligo-DNA are fixed in high density, i.e., an oligo-DNA chip, by attaching the iminecalixarene derivative compound of said formula 2 to a gold substrate or a glass substrate wherein an amine functional group is attached, and a preparation method thereof.

FIG. 1 schematically illustrates the process for preparing a self-assembled monolayer on the glass substrate of the iminecalixarene derivative of the present invention.

A detailed method for preparing a self-assembled monolayer of the iminecalixarene derivative on a glass substrate wherein an amine functional group is attached is as follows:

First, the glass substrate (glass slide glass) wherein said amine functional group is attached is prepared in the form of a glass substrate (amine slide glass or amine chip) having an amine terminal group through a chemical reaction on the surface of a glass substrate having sufficient silanol (—Si—OH) functional groups according to the method of the following cited reference 2 [Cited Reference 2: Langmuir, 1997, Vol 13, pp 4305-4308; Langmuir, 1996, Vol 12, pp 5338-5342]. The thus-prepared glass substrate wherein the amine functional group is attached and the compound of formula 2 are added to a mixed solution of chloroform and THF dissolved in a concentration of 0.1-5 mM ($CHCl_3$:THF=9:1). After 1~5 hours, it is washed with chloroform, acetone and ethanol, in that order, and dried, and then an iminecalixarene self-assembled monolayer as FIG. 1 is completed. The formation of said monolayer is confirmed using infrared external reflection spectroscopy. As said glass substrate, all types of slide glasses on the market can be used. As for the imine bonding used in the bonding, the bonding can break down when kept in water for a long period of time. However, since living substances such as oligo-DNA are mostly prepared by being dissolved in a buffer solution with a pH of between 7~8, it has been confirmed that there is no problem in using it immediately in the form of an imine bonding when being used for such purposes.

Figure 2:
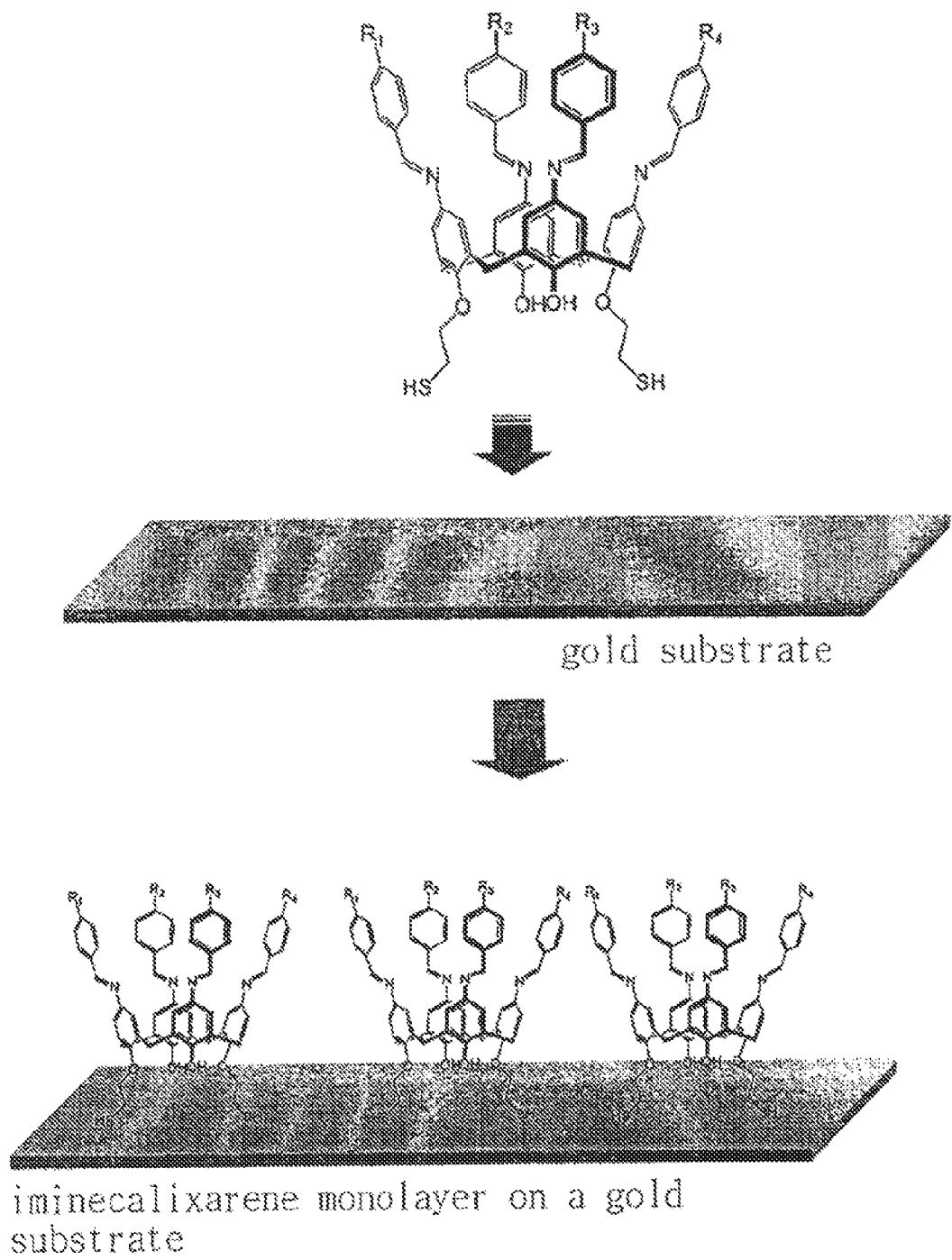
FIG. 2 is a schematic diagram of the preparation process of the self-assembled monolayer on the gold substrate of the iminecalixarene derivative of the present invention.

FIG. 2 schematically illustrates the process for preparing a self-assembled monolayer on the gold substrate of the iminecalixarene derivative of the present invention.

A detailed method for preparing a self-assembled monolayer of an iminecalixarene derivative on a gold substrate is as follows:

A solution is prepared by dissolving the compound, wherein thiol is attached, among the compounds of formula 2 in an organic solvent such as chloroform ($CHCl_3$), etc. in a concentration of 0.1-5 mM. After putting the gold substrate into the thus-prepared solution and leaving it for 1~5 hours, it is taken out and washed with chloroform, acetone and water, in that order, and dried, and then an iminecalixarene derivative self-assembled monolayer as FIG. 2 is completed. Said gold substrate may be any type of gold thin film; however, in general, a substrate vacuum plated with gold in a thickness of 50-200 nm after vacuum plating with chromium (Cr) or titanium (Ti), etc. in 2-10 nm, glass, fused silica, silicon wafer, plastic substrate, etc., is preferable. In general, the thus-prepared gold substrate is used after being put in a piranha solution (strong sulfuric acid:30% hydrogen peroxide=3:1) for about 1 minute immediately before use, and then being washed with purified water and dried by blowing nitrogen. The formation of said monolayer is confirmed using infrared external reflection spectroscopy.

Also, the present invention provides a method for preparing oligo-DNA chips by fixing an oligo-DNA wherein consecutive guanine bases are attached on said solid substrate by multi-molecular recognition, and an oligo-DNA chip prepared by the method.

More particularly, the present invention provides a fixing method of oligo-DNA by multi-molecular recognition by molecularly recognizing consecutive guanine functional groups through four nitrogen atoms of said iminecalixarene derivative.

The fixing method of the present invention of oligo-DNA forms the basis of all types of analysis methods using oligo-DNA, which is a novel method on which no similar researches have been published all over the world until now.

Figure 3:
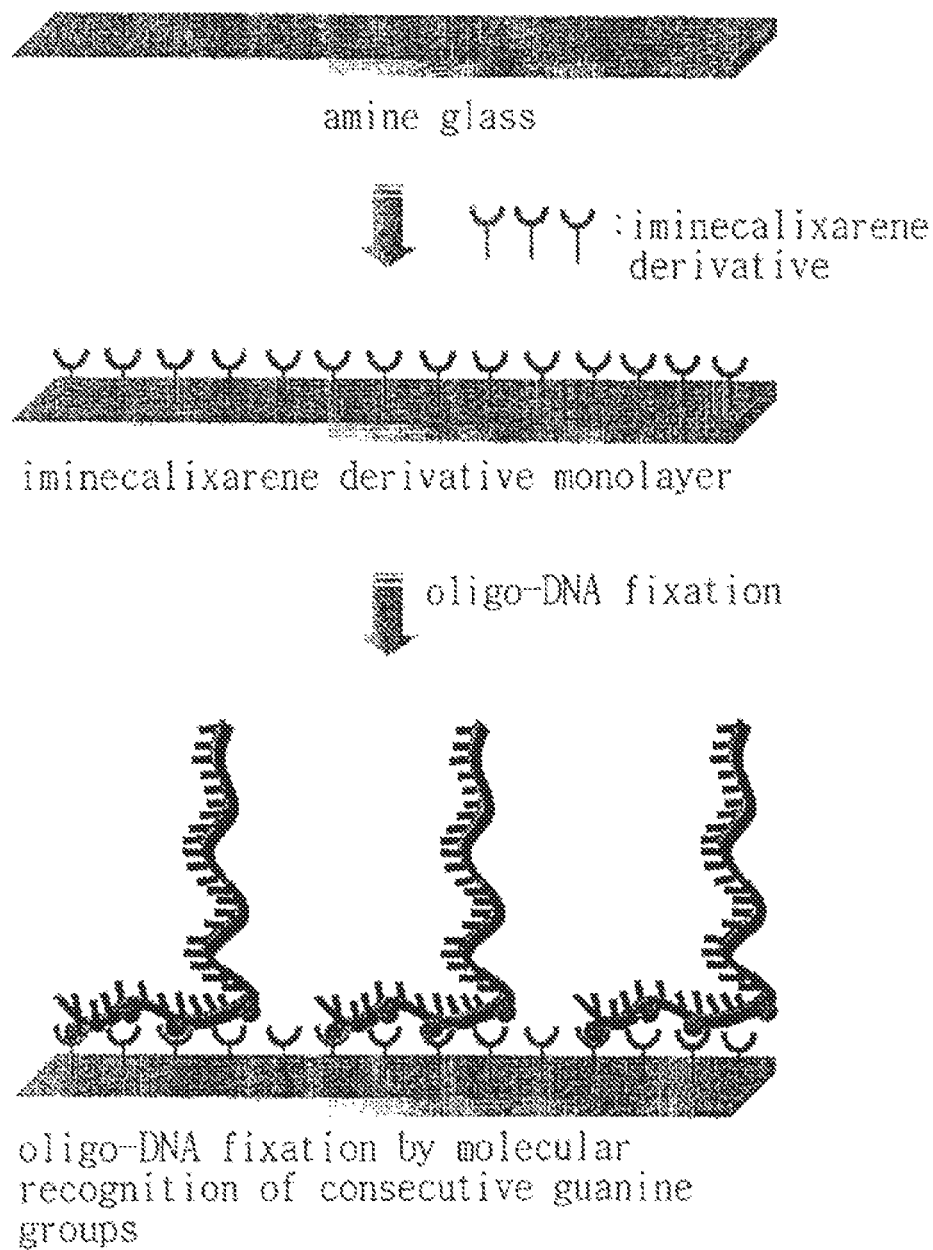
FIG. 3 is a schematic diagram of the fixing method of oligo-DNA having consecutive guanine bases of the present invention.

FIG. 3 is a schematic drawing of the fixing method of oligo-DNA having consecutive guanine groups of the present invention.

The oligo-DNA having consecutive guanine groups used for the fixing is 5'-GGG GGG GGG AAA TCA ACC CAC AGC TGC A-3' (SEQ ID NO. 1). The fluorescent attached c-DNA to be combined therewith is 5'-Cy3-GT GCA GCT GTG GGT TGA TT-3' (SEQ ID NO. 2), which has a DNA sequence complementary with the fixed oligo-DNA. Here, the density of the fixed oligo-DNA is measured by attaching the fluorescent substance Cy-3 (Telechem, U.S.A.) to the terminal group so that fluorescence is shown only at the position it is attached. After dissolving oligo-DNA in a 500 mM KCl solution comprising 15% glycerol in a concentration of 54 μg/ml (6.75 pmol/μl), the oligo-DNA is fixed by being coated on an iminecalixarene monolayer prepared by using a micro array purchased from Proteogen Co. (Korea) in a diameter of about 150 um. About 1-4 hours later, it is washed with a 2×SSC (1×SSC=sodium sitrate 15 mM+NaCl 150 mM) solution comprising 0.1% SDS (sodium dodecyl sulfate), and washed with a 0.1×SSC solution for 3 minutes and dried to be prepared. It has been confirmed that the prepared oligo-DNA monolayer does not show any change that can be measured for at least 6 months.

Figure 4:
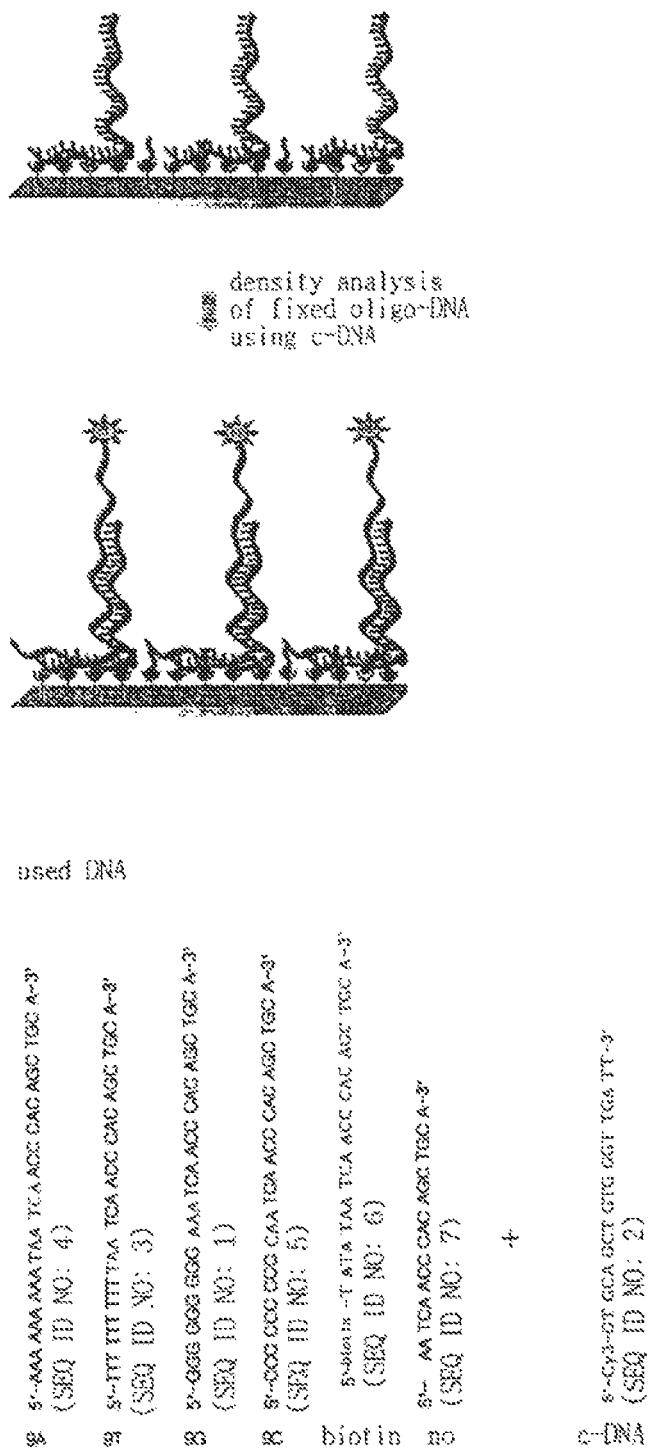
FIGS. 4 & 5 illustrate the process of selectively fixing only oligo-DNA having consecutive guanine bases, and show the result of analyzing the density of fixed oligo-DNA using c-DNA wherein fluorescence is attached.
Figure 5:
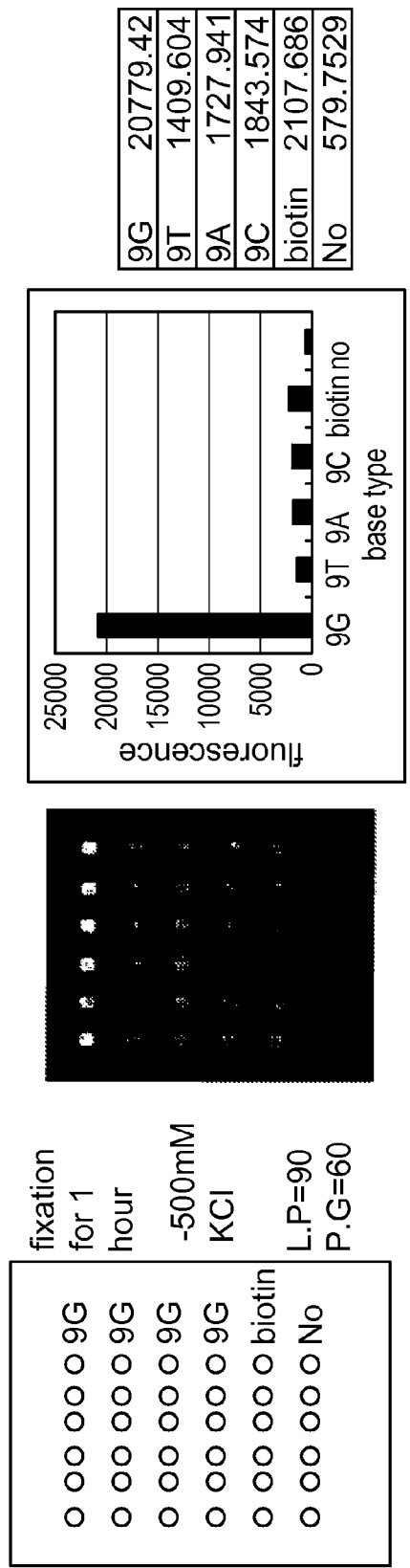

FIGS. 4 & 5 are schematic drawings showing fluorescent analyses of the oligo-DNA density at the oligo-DNA monolayer of the present invention.

The oligo-DNA having consecutive guanine groups used for the fixation to the oligo-DNA monolayer prepared in FIG. 3 is 5'-GGG GGG GGG AAA TCA ACC CAC AGC TGC A-3' (SEQ ID NO. 1). The fluorescent attached c-DNA to be combined therewith is 5'-Cy3-GT GCA GCT GTG GGT TGA TT-3' (SEQ ID NO. 2), which has a DNA sequence complementary with the fixed oligo-DNA. Also, the density of the fixed oligo-DNA is measured by attaching the fluorescent substance Cy-3 (Telechem, U.S.A.) to the terminal group so that fluorescence is shown only at the position it is attached. The monolayer is coated with 60 μl of the mixed solution of 4×SSC+0.002% SDS+50% glycerol wherein the c-DNA fluorescent attached to the fixed oligo-DNA is dissolved in a concentration of 0.17 nmol/ml, and the DNA is hybridized for 30 minutes at 50° C. Then, after first washing it with a 4×SSC solution comprising 0.1% SDS at room temperature, and second washing it with a 4×SSC solution, it is dried. The results can be confirmed using a scanner (GSI lite, U.S.A.).

As oligo-DNAs used for fixation, an oligo-DNA having the following DNA sequences respectively having 9 consecutive A, T, C, G base sequences, an oligo-DNA wherein biotin, a functional group similar to guanine, is attached, and an oligo-DNA having no consecutive base sequences, are used. Accordingly, it has been confirmed through an experiment that only consecutive guanine bases are selectively fixed. The DNA sequences used in the fixing comparison are as follows:

```
                                                 (SEQ ID NO. 1)
9G 5'-GGG GGG GGG AAA TCA ACC CAC AGC TGC A-3'

(SEQ ID NO. 3)
9T 5'-TTT TTT TTT TAA TCA ACC CAC AGC TGC A-3'

(SEQ ID NO. 4)
9A 5'-AAA AAA AAA TAA TCA ACC CAC AGC TGC A-3'

(SEQ ID NO. 5)
9C 5'-CCC CCC CCC CAA TCA ACC CAC AGC TGC A-3'
```

-continued

```
                                              (SEQ ID NO. 6)
biotin 5'-biotin-T ATA TAA TCA ACC CAC AGC TGC A-3'

(SEQ ID NO. 7)
no     5'-AA TCA ACC CAC AGC TGC A-3'
```

The c-DNA combined by being hybridized with them is synthesized to have complementary base sequence.

```
                                              (SEQ ID NO. 2)
       5'-Cy3-GT GCA GCT GTG GGT TGA TT-3'
```

At the same time, it was made possible to relatively analyze the density of the c-DNA attached, i.e. the density of the fixed oligo-DNA wherein c-DNA is attached, by attaching the fluorescent substance (Cy3) with the fluorescent scanner. According to the actual experimental results, after coating and fixing each oligo-DNA in the above stated condition in the same manner, the c-DNA is coated with three times the amount of the oligo-DNA that can be fixed on the surface in maximum, so that the c-DNA that is sufficiently fluorescent attached to all of the fixed oligo-DNA is combined therewith. Then, it is washed and dried to be analyzed with a fluorescent scanner.

The actual experimental results are the middle drawing of FIG. 5 which show the result in 6×6, and the results obtained from analyzing this fluorescence by numeral values and showing the analysis in a bar graph is the right drawing of FIG. 5. The actual experimental results show that the 9G oligo-DNA having 9 consecutive guanine groups present a fluorescence about 10 to 40 times higher than that of an oligo-DNA having different consecutive bases attached, or biotin attached, or not having a consecutive base attached. Said results show that only when there are consecutive guanine bases at the time of fixing oligo-DNA, an oligo-DNA is fixed on the surface of iminecalixarene to a level that can be analyzed.

Figure 6:
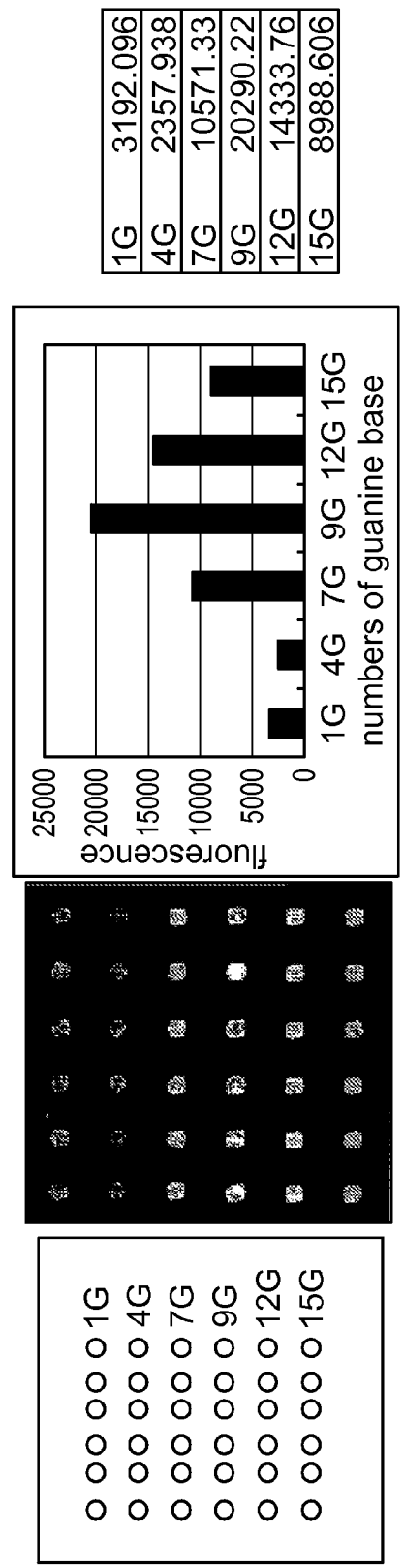
FIG. 6 shows that at least 7 consecutive guanine functional groups are required when fixing oligo-DNA to the iminecalixarene derivative self-assembled monolayer of the present invention. "12G" disclosed as SEQ ID NO: 32 and "15G" disclosed as SEQ ID NO: 33.

FIG. 6 shows that at least 7 consecutive guanine functional groups are essential for fixing oligo-DNA on the iminecalixarene derivative self-assembled monolayer of the present invention.

The oligo-DNA fixing condition is proceeded in the condition presented in FIG. 3, and c-DNA is hybridized according to the condition presented in the above using the fluorescent attached oligo-DNA used in FIG. 4 as well.

```
                                              (SEQ ID NO. 8)
1G  5'-GAA TCA ACC CAC AGC TGC A-3'

(SEQ ID NO. 9)
4G  5'-GGG GAA TCA ACC CAC AGC TGC A-3'

(SEQ ID NO. 10)
7G  5'-GGG GGG GAA TCA ACC CAC AGC TGC A-3'

(SEQ ID NO. 1)
9G  5'-GGG GGG GGG AAA TCA ACC CAC AGC TGC A-3'

12G (SEQ ID NO: 32)                           (SEQ ID NO. 11)
5'-GGG GGG GGG GGG GAA TCA ACC CAC AGC TGC A-3'

15G (SEQ ID NO: 33)                           (SEQ ID NO. 12)
5'-GGG GGG GGG GGG GGG GAA TCA ACC CAC AGC TGC A-3'
                                              (SEQ ID NO. 2)
c-DNA 5'-Cy3-GT GCA GCT GTG GGT TGA TT-3'
(Cy-3 ; fluorescent substance)
```

The oligo-DNA is coated, washed and then dried in the same condition presented in the above. According to actual experimental results, after coating and fixing each oligo-DNA in the above stated condition in the same manner, the c-DNA is coated with three times the amount of the oligo-DNA that can be fixed on the surface in maximum, so that the c-DNA that is sufficiently fluorescent attached to all of the fixed oligo-DNA is combined therewith. Then, it is washed and dried to be analyzed with a fluorescent scanner.

The actual experimental results are the middle drawing of FIG. 6 which show the result in 6×6, and the results obtained from analyzing this fluorescence by numeral values and showing the analysis in a bar graph is the right drawing of FIG. 6. When the consecutive guanine base sequence is about 1 or 4, it shows a result that surface fixation is almost not performed. Also, it begins to show strong fluorescence when it has 7 consecutive guanines (7G), and shows the maximum fluorescence with 9 consecutive guanines (9G). At this time, when an oligo-DNA having 12 (12G) (SEQ ID NO: 32) and 15 (15G) (SEQ ID NO: 33) consecutive guanine bases, which are longer than that 9 consecutive guanine bases, is used, the fluorescence sensitivity starts to decrease. This result shows that 9 guanine bases is a level sufficient for the fixation by molecular recognition and that when a longer guanine base is used, in theory, fixing an oligo-DNA of 12G (SEQ ID NO: 32) requires about ⅓ of the space more than fixing an oligo-DNA of 9G, and as results, the fluorescence sensitivity reduces to a level of about ⅓. The oligo-DNA of 15G (SEQ ID NO: 33) requires about an additional ⅔ of the space more than that of 9G, and thus in theory, the amount to be fixed is reduced to a level of about ⅗, i.e. 60%, and in fact, the fluorescence sensitivity is reduced by about 55% as compared to 9G. Putting said results together, it can be understood that the number of consecutive guanines required for fixation is at least 7. Preferably, the number of said consecutive guanines is 7 to 15, more preferably, 9 to 12, and most preferably 9.

FIG. 7 is the result of the competitive reaction using an imidazole functional group having a similar structure in order to verify that the guanine group is selectively recognized by molecular recognition at the time of fixing oligo-DNA on the iminecalixarene derivative self-assembled monolayer of the present invention.

FIG. 7 shows the result that consecutive guanine bases are fixed by molecular recognition, which is obtained from a research by performing fixation by including an imidazole capable of molecular recognition similar to guanine base. Since imidazole has relatively weak molecular recognition within iminecalixarene than guanine base, molecular recognition has been subjected to competitive reaction using a concentration higher than that of the oligo-DNA to be fixed. Fixation is performed in the same fixation condition as in FIG. 3 and the method for measuring fluorescence sensitivity is proceeded using c-DNA in the same method used in FIG. 4. The left drawing of FIG. 7 shows the actual experimental results, and the right chart shows the decrease in the fluorescence sensitivity depending on the concentration of imidazole used for the competitive reaction of the fluorescence sensitivity. In fact, it shows a result that the decrease starts at a level of about 20 mM and it decreases to half at a level of 30 mM and the fixing of oligo-DNA is almost not performed at 100 mM and above. Such results show that the fixation of oligo-DNA is performed by the multi-molecular recognition of 9 consecutive guanine bases within the iminecalixarene derivative.

Such results as above show that the iminecalixarene derivative self-assembled monolayer performs irreversible fixation of 9 consecutive guanine bases by multi-molecular recognition. In particular, the amount of the fixed oligo-DNA presented by fluorescent analysis shows a fixing density 5~30 times higher than that of the conventionally known method.

As such, the present invention provides a novel fixing method of oligo-DNA capable of securing space by remarkably reducing the hybridization time required for c-DNA bonding to within 1~2 hours, which used to take at least 12 hours, by providing as much space (2.5-3.5 nm) as required for the c-DNA having at least hundreds of base sequences to come down to the bottom part of the oligo-DNA for a strong bonding with the fixed oligo-DNA, at the time of analyzing a gene having a specific base sequence for the purpose of diagnosis or research, etc. by a space of its length (2.5-3.5 nm) while the consecutive guanine bases are fixed on the surface of the monolayer.

As another aspect of the present invention, the novel aminocalixarene derivative of the present invention has the structure of the following formulae 5~8. Said aminocalixarene derivative is a compound essential to the self-assembled monolayer used in the fixing method of oligo-DNA having consecutive guanine groups.

[Formula 5]

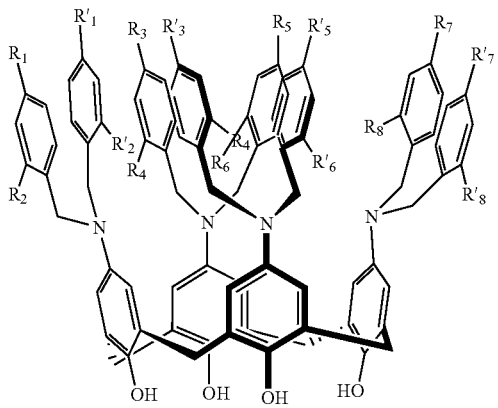

(wherein, $R_1, R_2, R_3, R_4, R_5, R_6, R_7, R_8, R'_1, R'_2, R'_3, R'_4, R'_5, R'_6, R'_7, R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR, and in said —COOR, R represents —$CH_3$ or —$C_2H_5$.)

[Formula 6]

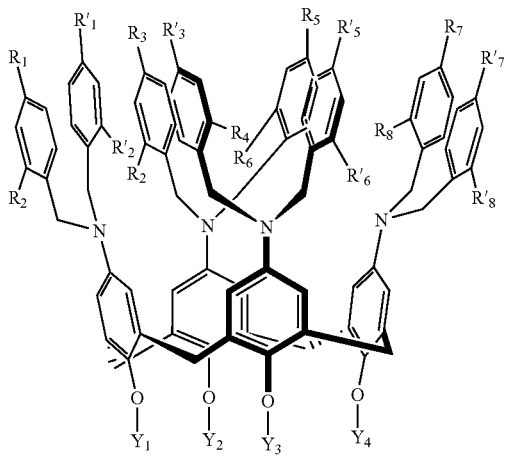

(wherein, $R_1, R_2, R_3, R_4, R_5, R_6, R_7, R_8, R'_1, R'_2, R'_3, R'_4, R'_5, R'_6, R'_7, R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR, and in said —COOR, R represents —$CH_3$ or —$C_2H_5$. Also, said $Y_1, Y_2, Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —$(CH_2CH_2O)_m$—$CH_2CH_2$—SH, —$(CH_2)_m$—$C_6H_4$—$(CH_2)_c$—Z, and —CO—$(CH_2)_m$-1-$C_6H_4$—$(CH_2)_c$—Z (wherein, n=2~15, m=1~10, c=0~10, Z=—SH, —CHO, —COOH, —$NH_2$, and —$C_6H_4$— and $C_6H_5$ are defined as a phenyl group).)

[Formula 7]

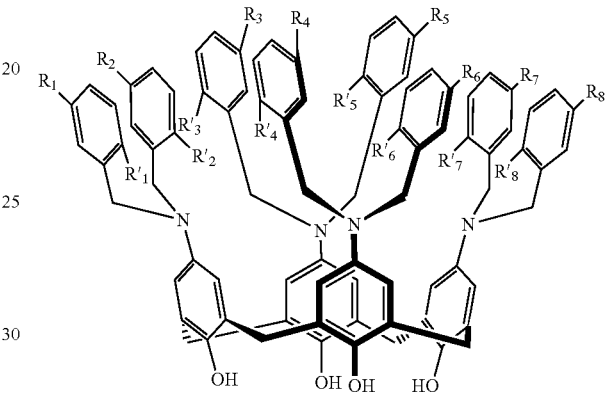

(wherein, $R_1, R_2, R_3, R_4, R_5, R_6, R_7, R_8, R'_1, R'_2, R'_3, R'_4, R'_5, R'_6, R'_7, R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR, and in said —COOR, R represents —$CH_3$ or —$C_2H_5$.)

[Formula 8]

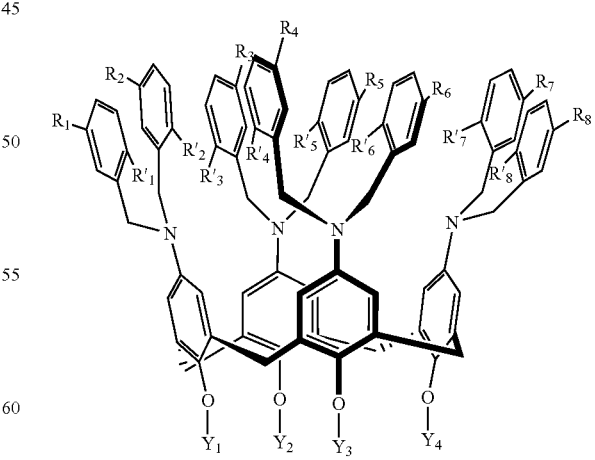

(wherein, $R_1, R_2, R_3, R_4, R_5, R_6, R_7, R_8, R'_1, R'_2, R'_3, R'_4, R'_5, R'_6, R'_7, R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —OC$_6$H$_5$, —OC$_6$H$_4$CH$_3$, —OC$_6$H$_4$C(CH$_3$)$_3$, —OC$_6$H$_4$CF$_3$, —OC$_6$H$_4$Cl, —OCOCH$_3$, —NHCOCH$_3$, —CONHCH$_3$, —CN, COOH, and —COOR, and in said —COOR, R represents —CH$_3$ or —C$_2$H$_5$. However, the case where R$_1$, R$_2$, R$_3$, R$_4$, R$_5$, R$_6$, R$_7$, R$_8$, R'$_1$, R'$_2$, R'$_3$, R'$_4$, R'$_5$, R'$_6$, R'$_7$, R'$_8$ are —H at the same time is excluded. Also, said Y$_1$, Y$_2$, Y$_3$ and Y$_4$ are independently selected from the group consisting of —H, —(CH$_2$)$_n$—CH=O, —(CH$_2$)$_n$—SH, —(CH$_2$CH$_2$O)$_m$—CH$_2$CH$_2$—CH=O, —(CH$_2$CH$_2$O)$_m$—CH$_2$CH$_2$—SH, —(CH$_2$)$_m$—C$_6$H$_4$—(CH$_2$)$_c$—Z, and —CO—(CH$_2$)$_m$-1-C$_6$H$_4$—(CH$_2$)$_c$—Z (wherein, n=2~15, m=1~10, c=0~10, Z=—SH, —CHO, —COOH, —NH$_2$, and —C$_6$H$_4$— and C$_6$H$_5$ are defined as a phenyl group).)

The present invention provides a method for preparing the aminocalixarene derivative compounds of said formulae 5~8.

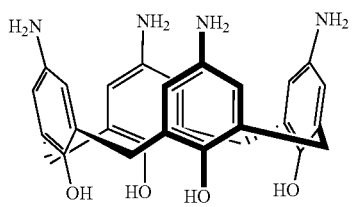

[Formula 9]

The tetraminocalix[4]arene of said formula 9 is synthesized by a reduction reaction after transforming calix[4]arene to tetranitrocalix[4]arene according to the method of said cited reference 1.

The aminocalixarene derivative compounds of formulae 5 & 7 of the present invention are synthesized by having the tetraminocalix[4]arene of formula 9 synthesized by said known method as a starting material and reacting the amine functional group of formula 9 with benzyl chloride or benzyl bromide derivatives according to example 13 below. Alternatively, after reacting the functional group of formula 9 with aromatic aldehyde in accordance with the method of the following example 16 and then performing the reduction reaction using a reducing agent, it is reacted with benzyl chloride or benzyl bromide derivatives to synthesize the aminocalixarene derivative of formulae 5 & 7.

The aminocalixarene derivative compounds of formulae 6 & 8 of the present invention, wherein aldehyde or thiol is attached by attaching the following —OH, i.e., the 1$^{st}$ and 3$^{rd}$ alcohol functional groups among the alcohol functional groups to the alkyl group terminal, are synthesized by reacting the compounds of formulae 5 & 7 with the compound having functional groups such as aldehyde wherein halogen is attached to the terminal group in accordance with the following examples 17~19.

Also, the present invention provides a method for preparing an oligo-DNA chip substrate for preparing an oligo-DNA monolayer capable of fixing all types of oligo-DNA in high density by attaching the aminocalixarene derivative of said formula 6 or 8 to a gold substrate or a solid substrate such as glass, etc. wherein various functional groups, such as amine, etc., are attached.

Also, the present invention provides a self-assembled monolayer solid substrate prepared by attaching through imine and amine bondings an aminocalixarene derivative wherein an aldehyde functional group is attached to the terminal group among the aminocalixarene derivatives of said formula 6 or 8, to a solid substrate selected from the group consisting of glass, silicon wafer and crystal wherein the amine functional group is attached.

Also, the present invention provides a self-assembled monolayer solid substrate prepared by attaching, through a chemical bonding selected from ester, ether or amide bonding using an aminocalixarene derivative wherein an aldehyde functional group is attached to the terminal group among the aminocalixarene derivatives of said formula 6 or 8, to a solid substrate selected from the group consisting of glass, silicon wafer and quartz crystal wherein the amine functional group is attached.

Also, the present invention provides a method for preparing an oligo-DNA monolayer, i.e., an oligo-DNA chip, by fixing oligo-DNA having consecutive bases by irreversible molecular recognition without any treatment of said oligo-DNA chip substrate.

Figure 8:
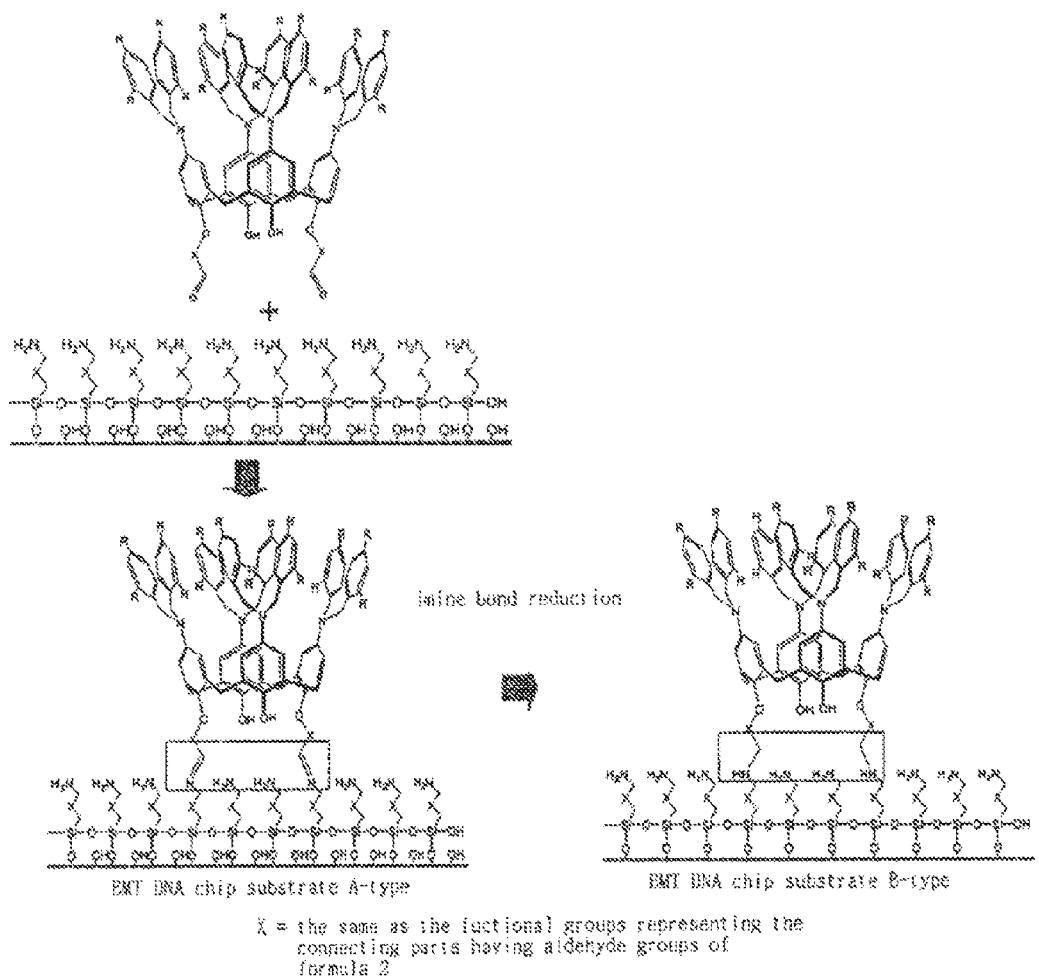
FIG. 8 is a schematic diagram of the preparation process of the self-assembled monolayer on the glass substrate of the aminocalixarene derivative of the present invention.

FIG. 8 schematically illustrates the process for preparing a self-assembled monolayer on a solid substrate such as glass, silicon wafer, fused silica of the aminocalixarene derivative of the present invention.

The detailed method for preparing the self-assembled monolayer of an aminocalixarene derivative on a glass substrate wherein an amine functional group is attached is as follows:

The glass substrate (glass slide glass) where the earlier used amine functional group is attached is prepared in the form of a glass substrate (amine slide glass, or amine chip) having an amine terminal group through a chemical reaction on the surface of a glass substrate having sufficient silanol (—Si—OH) functional group on the surface according to the method disclosed in said cited reference 2. Thus prepared glass substrate where the amine functional group is attached is added to a mixed solution of chloroform and THF wherein the compound of formula 6 or 8 is dissolved in a concentration of 0.1-5 mM (CHCl$_3$:THF=9:1). After 1~5 hours, it is washed with chloroform, acetone and ethanol, in that order, and dried, and then the self-assembled monolayer of the aminocalixarene derivative as in FIG. 8, i.e., a BMT DNA chip substrate type A is completed. The formation of said monolayer is confirmed using infrared external reflection spectroscopy. For said glass substrate, all types of slide glass or glass generally on the market can be used. As for the imine bonding used in the bonding, the bonding may break down when kept in water for a long period of time. However, since living substances such as oligo-DNA are mostly prepared by being melt in a buffer solution wherein the pH is between 7~8, it has been confirmed through research results that there is no problem in using it immediately in the form of an imine bonding when being used for such purposes.

If the prepared BMT DNA chip substrate type A is put in an organic solvent where a reducing agent such as BH$_3$-THF or 1-5% NaBH$_4$ is dissolved as in FIG. 8 for 1~10 minutes, the imine is reduced to an even stronger amine and thus, excellent stability can be guaranteed for long period storage or preparation of a DNA chip in a different pH range.

Figure 9:
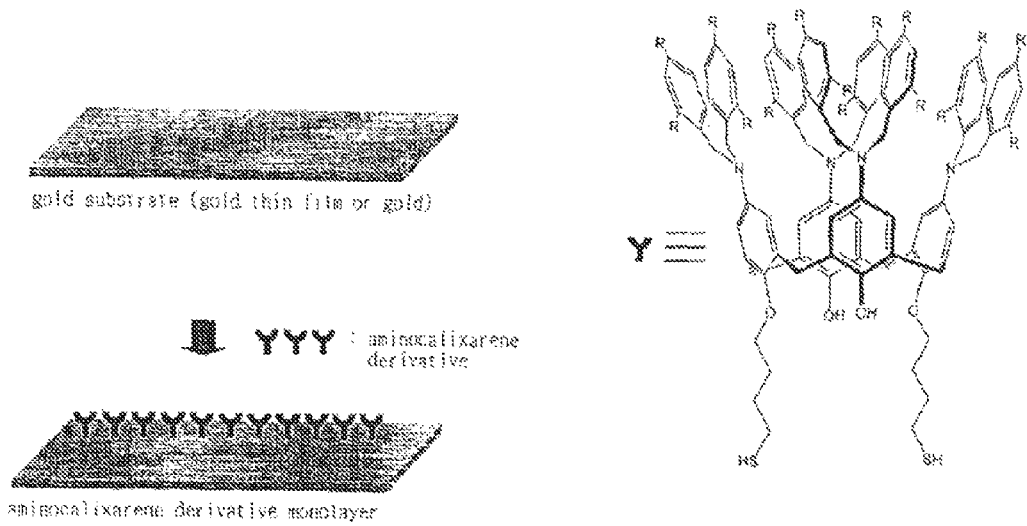
FIG. 9 is a schematic diagram of the preparation process of the self-assembled monolayer on the gold substrate of the aminocalixarene derivative of the present invention.

FIG. 9 schematically illustrates the process for preparing the self-assembled monolayer of the aminocalixarene derivative of the present invention on a gold substrate.

A detailed method for preparing the self-assembled monolayer of an aminocalixarene derivative on a gold substrate is as follows:

A solution is prepared by dissolving a compound wherein thiol is attached among the compounds of formula 6 or 8 in the organic solvent such as chloroform (CHCl$_3$), etc. in a concentration of 0.1-5 mM. After putting a gold substrate into the thus-prepared solution and leaving it for 1~5 hours, it is taken out and washed with chloroform, acetone and water, in that order, and dried, and then the self-assembled monolayer of aminocalixarene derivative as in FIG. 9 is completed. Said gold substrate may be any type of gold thin film; however, in general, a substrate vacuum plated with gold in a thickness of 50-200 nm after vacuum plating with chromium (Cr) or titanium (Ti), etc. in 2-10 nm, glass, fused silica, silicon wafer, plastic substrate, etc. is preferable. It is preferable to put the thus-prepared gold substrate in a piranha solution (strong sulfuric acid:30% hydrogen peroxide=3:1) for about 1 minute immediately before use, and then wash it with purified water and dry it by blowing nitrogen. The formation of said monolayer is confirmed using infrared external reflection spectroscopy.

Also, the present invention provides a method for preparing oligo-DNA chips by fixing an oligo-DNA wherein consecutive guanine bases are attached on said solid substrate by multi-molecular recognition and an oligo-DNA chip prepared by the method.

More particularly, the present invention provides a fixing method of oligo-DNA by multi-molecular recognition by molecularly recognizing consecutive guanine functional groups through four nitrogen atoms of said aminocalixarene derivative.

The fixing method of the present invention is the fundamental technology providing a technology for preparing all types of bio chips using an oligo-DNA, which is a novel method wherein no research results similar thereto have been published all over the world until now.

Figure 10:
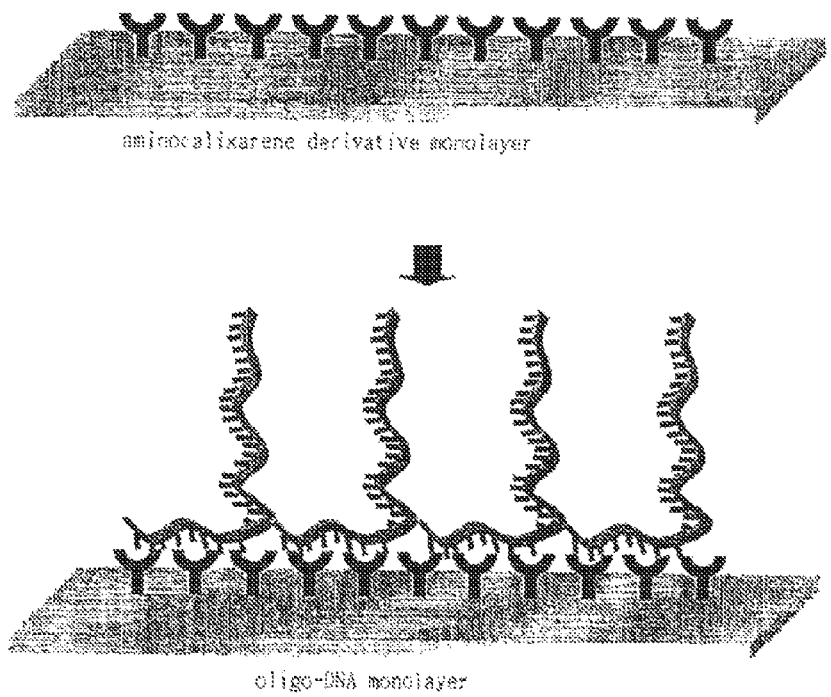

FIGS. 10 & 11 are a schematic drawing of a technology of preparing a high density oligo-DNA chip by voluntary molecular recognition, and a diagram for theoretically calculating the number of aminocalixarene derivatives constituting a monolayer. It is an actual experimental result of comparing the actual concentration of the oligo DNA with the maximum concentration of the oligo-DNA that can be fixed on the aminocalixarene derivative monolayer that has been theoretically calculated in addition.

The theoretical maximum amount of fixed oligo-DNA is calculated using the following equation. The diameter of the aminocalixarene obtained by the X-ray determination method is 2.1-2.2 nm. The number of molecules required when these are self-assembled on the surface as a monolayer is the same as the area of two triangles made by the lines connecting the centers of three aminocalixarene derivatives. Therefore, the area one calixarene derivative occupies on the surface can be obtained by the following equation:

[Equation]

$$2.1\ nm \times 2.1\ nm \times \sin 60° = 3.82 \times 10^{-14}\ cm^2$$

Therefore, the number of aminocalixarene derivatives present in each 1 cm$^2$ is $1/3.82 \times 10^{-14}$ cm$^2$=$2.62 \times 10^{13}$=43.5 pmol/cm$^2$. Since the area of 6~7 aminocalixarene derivatives combined is used to fix one oligo-DNA, the maximum oligo-DNA density for fixation is 43.5/(6~7) pmol/cm$^2$=6.2~7.25 pmol/cm$^2$. After hybridizing the oligo-DNA 5'-GGG GGG GGG AAA TCA ACC CAC AGC TGC A-3' for fixation (SEQ ID NO. 16) with c-DNA 5'-cy3-GT GCA GCT GTG GGT TGA TT-3' (SEQ ID NO. 19) fluorescently attached to the oligo-DNA chip fixed in maximum density according to the method of example 24, the result of measuring the fluorescent sensitivity using the fluorescent scanner (GSI, U.S.A.) after washing and drying it according to the method of example 13 is shown in the hybridization result of 2) of FIG. 11. As a result of measuring similar fluorescent sensitivity by using a fluorescent scanner after drying the same c-DNA 5'-cy3-GT GCA GCT GTG GGT TGA TT-3' (SEQ ID NO. 19) used in the hybridization in various concentrations, a fluorescent sensitivity of a similar level can be obtained when it is dried after being coated in a concentration of 3.8 pmol/cm$^2$, which is a half level of the amount theoretically calculated. The results are shown in the results of drying the fluorescent attached oligo-DNA of 1) of FIG. 11. Such results show that the BMT oligo-DNA chip substrate developed according to the present invention can prepare an oligo-DNA chip by fixing the oligo-DNA close to its theoretical maximum value, and can obtain about 50% of the maximum fluorescence even in hybridization for 30 minutes, and that it is the world first oligo-DNA chip preparation technology at once enabling ultra-high speed hybridization and realizing high density fixation technology.

Figure 12:
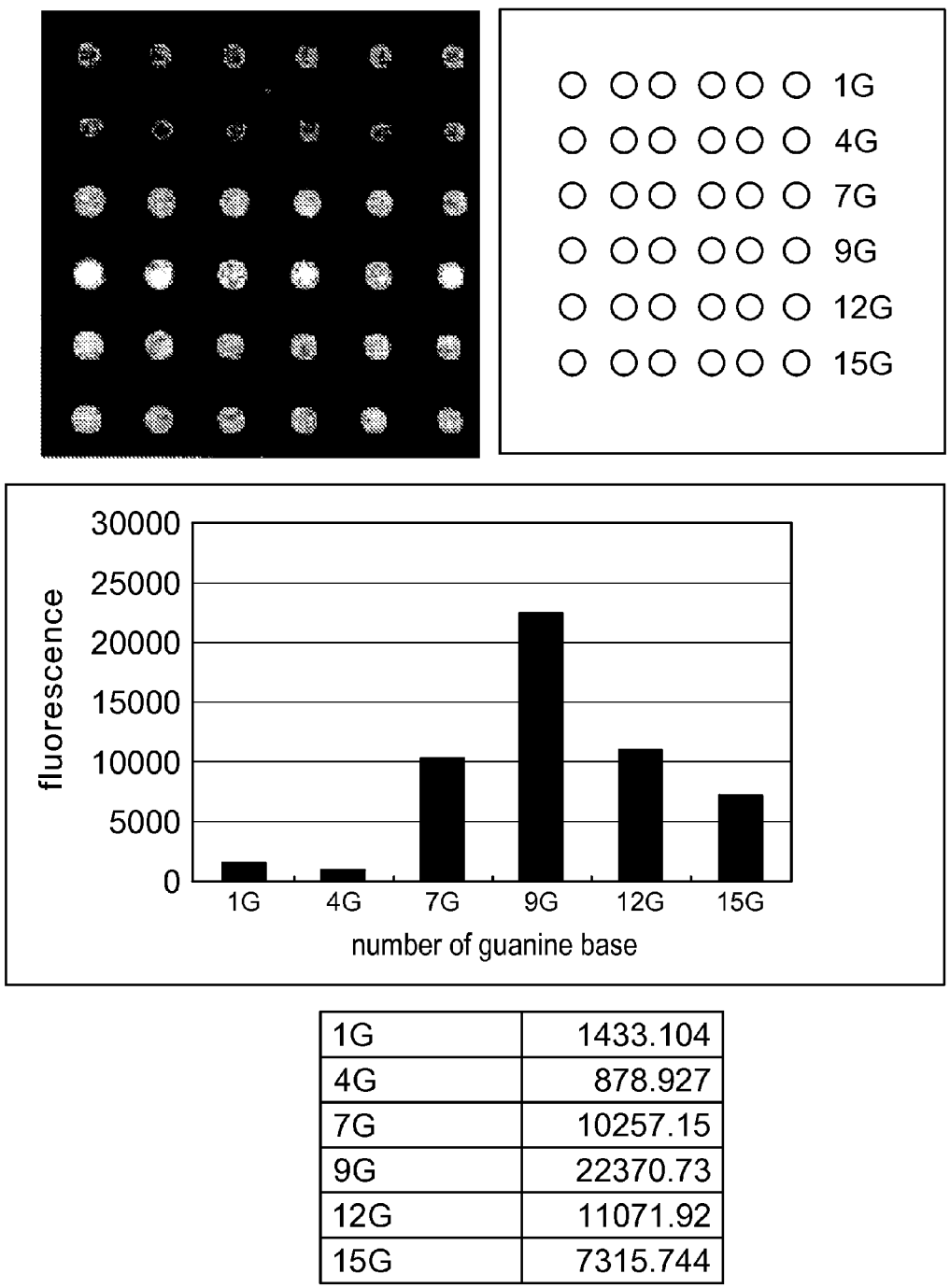
FIG. 12 is actual experimental results for determining the optimum number of consecutive guanine bases for fixation of maximum density. "12G" disclosed as SEQ ID NO: 32 and "15G" disclosed as SEQ ID NO: 33.

FIG. 12 is the result of an analysis using a fluorescent scanner (GSI, U.S.A.) after fixing an oligo-DNA (6.75 nmol/mL, 1 nL) of a concentration that is 5 times according to example 22 by using an oligo-DNA having the same base sequence wherein guanine bases are consecutively attached, hybridizing it according to example 22, washing and drying it in order to find the optimum number of consecutive bases. In the experiment of FIG. 12, a DNA having a base sequence shown in Table 4 is used, and in the hybridization, the fluorescent attached c-DNA of Table 4 is used.

The actual experiment results are scan data shown in the middle of FIG. 12 which show its result in 6×6, and the result of analyzing this fluorescence with numeral values and showing it in a bar graph is at the bottom of FIG. 12. When the consecutive guanine base sequence is about 1 or 4, it shows a result that surface fixation is almost not performed. However, it starts to show strong fluorescence with 7 consecutive guanines (7G), and when it has 9 consecutive guanines (9G), it shows a fluorescence of a level twice as high as that of 7 consecutive guanines (7G). When an oligo-DNA having 12 (12G) (SEQ ID NO: 32) and 15 (15G) (SEQ ID NO: 33) consecutive guanine bases, which are longer than 9 consecutive guanine bases, is used, it shows a fluorescent sensitivity reduced to a level of ½, ⅓ of 9 consecutive guanine bases. This shows a result that 9 consecutive guanine bases is a level sufficient to fix an oligo DNA by molecular recognition and that when a longer guanine base is used, in theory, an oligo-DNA of 12G (SEQ ID NO: 32) requires a larger space than that of 9G, and as results, the fluorescence sensitivity decreases to a level of ½. The oligo-DNA of 15G (SEQ ID NO: 33) requires about an additional ⅔ of the space as compared to that of 9G, and thus the amount of oligo-DNA to be fixed is reduced to a level of about 30% and the fluorescence sensitivity is reduced to a level of about ⅓ of 9G. Putting said results together, it can be understood that the optimum number of consecutive guanines required for fixation is 9. If the number of consecutive guanines is less than 9G, it is possible that a sufficient level of irreversible oligo-DNA fixation by molecular recognition may not be performed. Also, it can be understood from the result that when the number of the consecutive guanine bases is greater than 9G, the area to be fixed is larger than 9G, which is the area required for fixation, and thus it results in reducing the number of oligo-DNAs actually being fixed.

Figure 13:
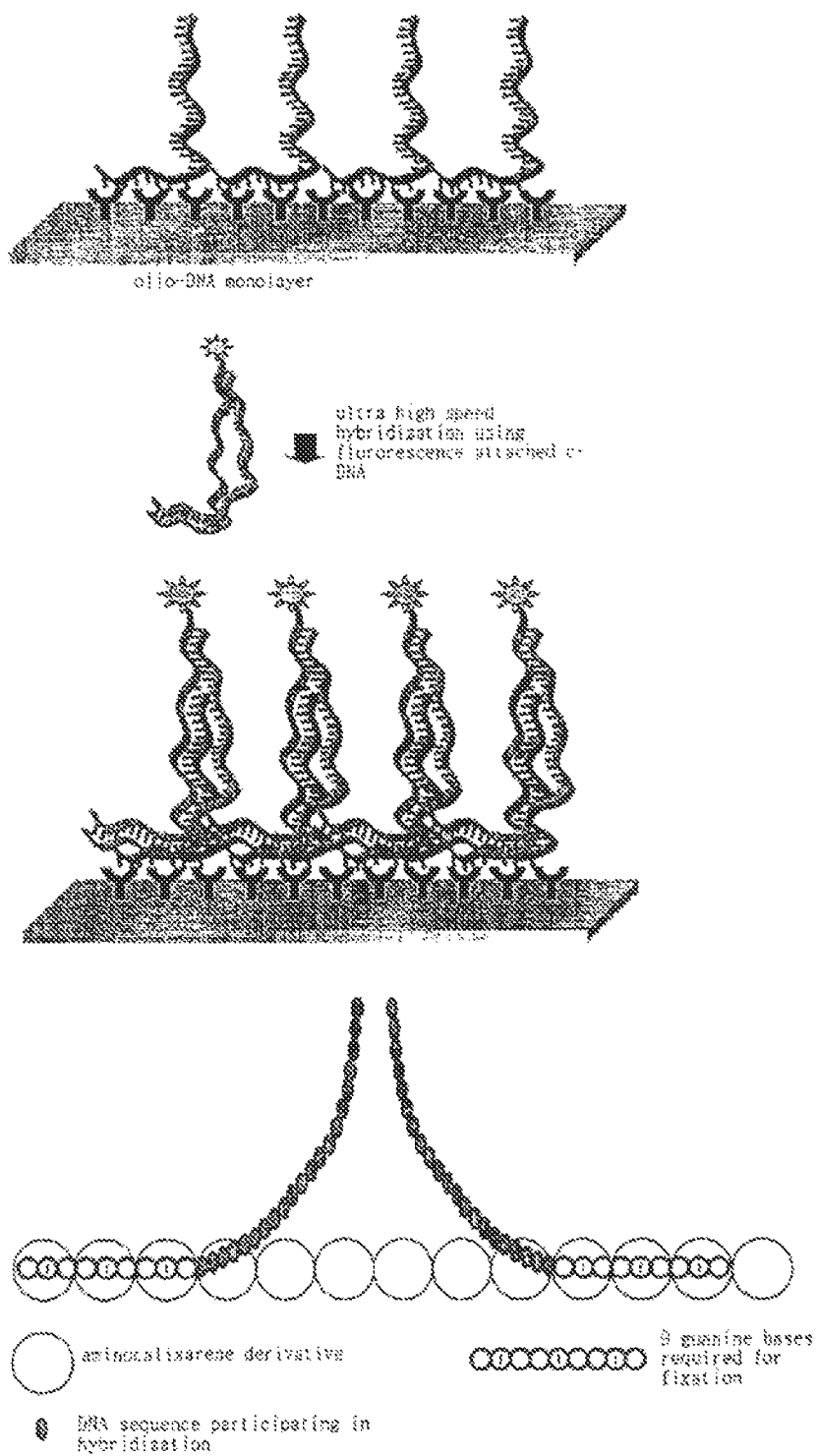
FIG. 13 is a diagram showing that it is possible for the c-DNA to access close to the bottom of the chip through the space secured between the fixed oligo-DNAs by securing appropriate space by consecutive bases at the time of fixing oligo-DNA.

FIG. 13 is a diagram showing that it is possible for the c-DNA to advance to the bottom of the chip through the space ensured between the fixed oligo-DNAs by securing a proper space by consecutive bases while fixing oligo-DNA and that a sufficient level of space for an ultra-high speed access is maintained. At the same time, it also shows that the surface area wherein 6~7 aminocalixarene derivatives are actually fixed is used when fixing oligo-DNA.

Figure 15:
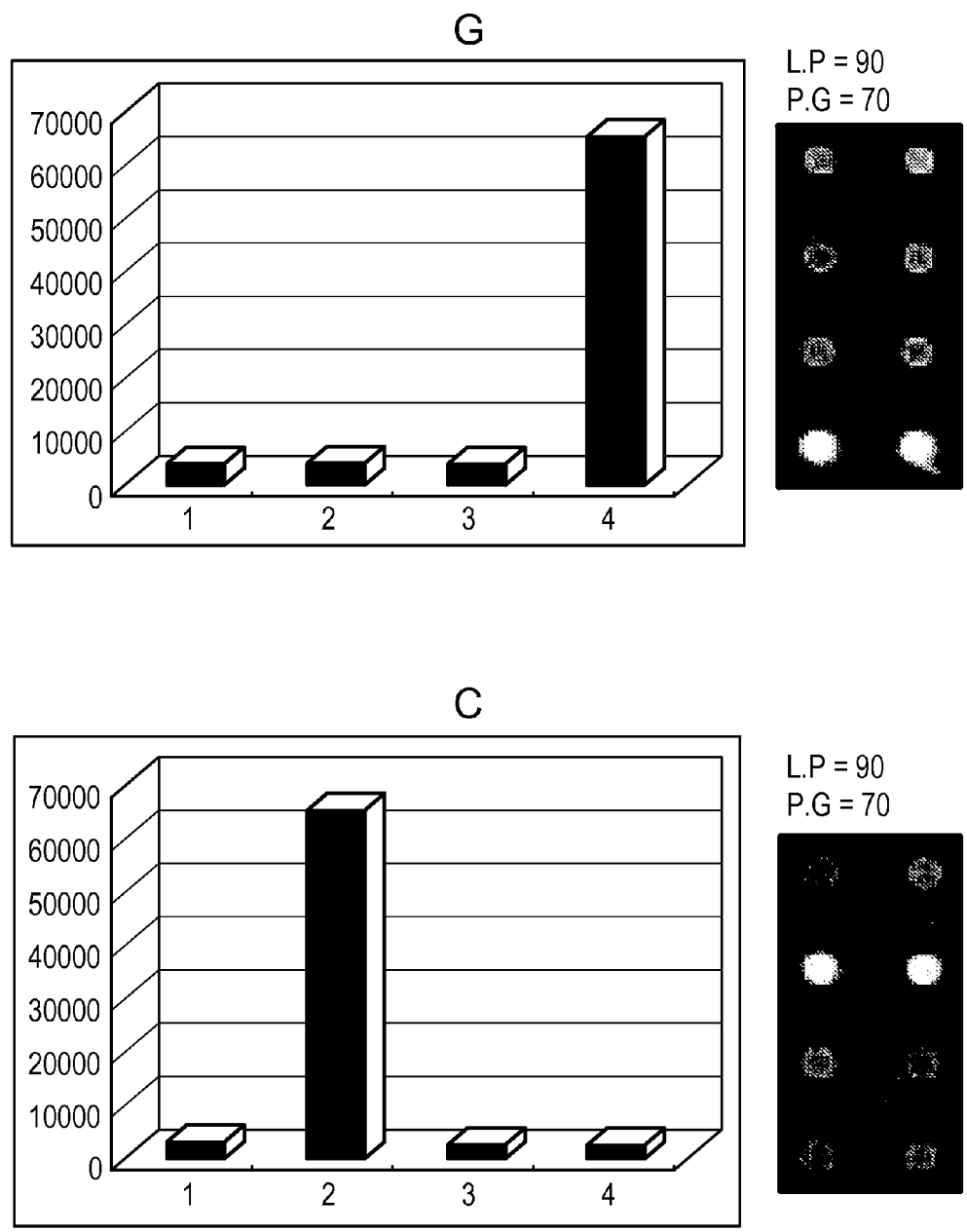

In FIGS. 14 & 15, the respective base sequences actually shown in Table 5 fix different A, C, G, T-type oligo-DNAs according to example 23. Then, after hybridizing the complementary c-DNA that can combine with these according to the hybridization with c-DNA for detecting DNA (Cy3-DNA) to which is attached the fluorescence of example 23, according to example 23, the fluorescent attached oligo-DNA of table 5 is used for fluorescent attachment according to example 23. Thereafter, it is washed and dried to analyze the fluorescence sensitivity by using the fluorescent scanner (GSI, U.S.A.). FIGS. 14 & 15 show that it is an oligo-DNA chip substrate capable of ultra-high speed hybridization that can distinguish and analyze the fluorescent sensitivity to an On-Off level even for a short hybridization time such as about 30 minutes, while distinguishing the SNP to an On-Off level. Also, it is a result showing that the technology for preparing an oligo-DNA chip as proposed in the present invention is a novel technology enabling an ultra-high hybridization and a convenient analysis of single nucleotide polymorphism (SNP) with high replication.

FIG. 16 is an actual competitive reaction result showing that guanine base alone selectively performs high speed fixation when compared with other bases. Using oligo-DNA (9G-1) wherein 9G is attached, which is not combined with the fluorescent attached oligo-DNA in table 6, in the same concentration according to example 25, it fixes DNA by coating the mixture mixing 4 types of oligo-DNA having a base sequence complementary with the fluorescent attached oligo-DNA (Cy-3-DNA) and 9A, 9G, 9T, 9C attached, in 1, 2, 4 times of concentration of oligo-DNA (9G-1) in the order as shown in FIG. 16. At this time, if the oligo-DNA wherein 9A, 9C, 9T, 9G are mixed in the same concentration is fixed faster than the oligo-DNA (9G-1), it will show fluorescence by combining with the fluorescent attached oligo-DNA in a hybridization proceeded in accordance with example 25, and if the oligo-DNA (9G-1) wherein 9G is attached is fixed faster, it is obviously expected that fluorescence will not be shown. According to the actual experimental results of FIG. 16, it can be confirmed that at the position of fixing 9G, the fluorescence sensitivity increases as the concentration of oligo-DNA increases at the time of fixation, so that at 9G-1: 9G=1:1, it shows a fluorescence sensitivity of about 50%, and at 1:4, it shows a fluorescence sensitivity of about 80%. At 9T, 9C, it can be confirmed that the fluorescence sensitivity increases very slightly, and even at 9A, it shows a slight fluorescence sensitivity only at a level 4 times the amount of 16G. Therefore, it shows that if an oligo-DNA wherein 9G is attached is used at the time of actual fixation, the part where there are bases which should be used in hybridization, i.e., the bases which should be used when being combined with c-DNA, does not participate in fixation, i.e., only the position where 9G is selectively attached can prepare an oligo-DNA that can be replicated by being combined with the aminocalixarene derivative monolayer proposed in the present invention in maximum density.

To sum up, the results show that an oligo-DNA chip can be prepared by having the aminocalixarene derivative self-assembled monolayer developed according to the present invention multimolecular recognize the consecutive guanine bases to irreversibly fix oligo-DNA on the monolayer surface, and that it is a fundamental technology for preparing oligo-DNA chip that can be replicated by always enabling fixation so that the amount of fixed oligo-DNA shown by fluorescent analysis is close to the theoretical maximum density.

Further, in the present invention, an oligo-DNA wherein consecutive guanine bases are fixed on the surface of the monolayer, while appearing to be fixed as in FIG. 13, is arranged securing space as long as said consecutive base. Such space enables the c-DNA having at least tens and hundreds of base sequences to easily approach the surface of the chip substrate freely in ultra-high speed when analyzing DNAs having a specific base sequence for purposes such as diagnosis or research, and thus enables ultra-high speed hybridization within a very short period of time such as 10 minutes 1 hour by having the maximum number of bases complementarily combined. Also, this invention is an invention suggesting a technology for preparing an oligo-DNA monolayer combined with a technology of sufficiently securing space between fixed DNAs so that even single nucleotide polymorphism can be simply diagnosed, i.e., a fundamental technology for preparing oligo-DNA chip.

Hereinafter, the present invention is described in more detail by the following examples. However, the present invention is not restricted thereto.

EXAMPLE 1

Preparation of 5,11,17,23-tetraminocalix[4]arene

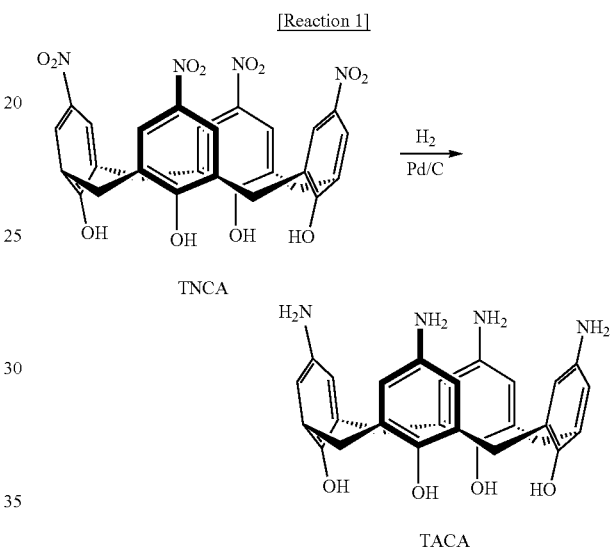

TNCA

TACA

A light yellow solid product, 5,11,17,23-tetraminocalix[4]arene (TACA) is obtained with the yield of 75% by having 5,11,17,23-tetranitrocalix[4]arene (TNCA) as a starting material and synthesizing it according to the synthesizing method presented in the following cited reference 3 [Cited Reference 3: Van Wagenigen, A. M. A.; Snip, E.; Verboom. W.; Reinhoudt, D. N.; Boerrigter, H.; Liebigs Ann/Recueil 1997. pp 2235-2245]. Said reaction is represented by reaction 1.

EXAMPLE 2

Preparation of
5,11,17,23-tetrabenzylimine-calix[4]arene

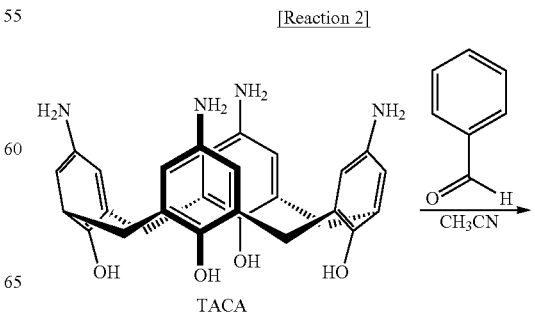

TACA

-continued

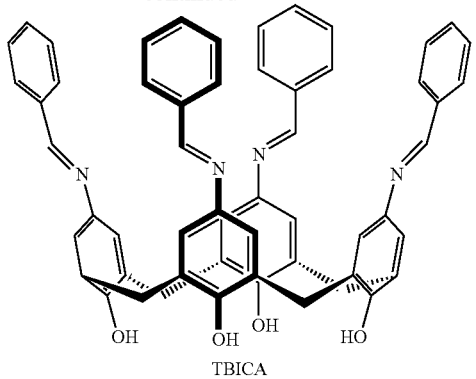
TBICA 500 mg of TACA (1.03 mmol) and 200 mg of anhydrous MgSO$_4$ are put into a dried round-bottom flask, and 150 ml of acetonitrile and 0.84 ml of benzaldehyde (8.24 mmol) are added at the same time, then they are mixed for two hours under nitrogen exchange at room temperature. After the reaction, it is filtered to remove the solid product, and then the solution is decompressed and the remaining solvent is removed. Then, after being completely dissolved in 5 ml of CH$_2$Cl$_2$, 30 ml of n-hexane is added to crystallize 5,11,17,23-tetrabenzylimine-calix[4]arene (TBICA) to a light-pink solid. TBICA (822 mg, yield 95.7%) is obtained by decompress filtering and removing the remaining solvent under reduced pressure. Said reaction is represented by reaction 2.

$^1$H NMR (300 MHz, CDCl$_3$): δ 10.15(s, 4H, OH), 8.34(s, 4H, N=CH), 7.82-7.78(m, 8H, Ar), 7.40-7.38(m, 12H, Ar), 7.01(s, 8H, Ar), 4.31(d, 4H, ArCH$_2$Ar, J=13 Hz), 3.63(d, 4H, ArCH$_2$Ar, J=13 Hz)

$^{13}$C NMR (300 MHz, CDCl$_3$): δ 159.26, 146.28, 136.40, 131.32, t128.86, 121.90, 32.47

EXAMPLE 3

Preparation of 5,11,17,23-tetrabenzyliminealkoxy-calix[4]arene

[Reaction 3]

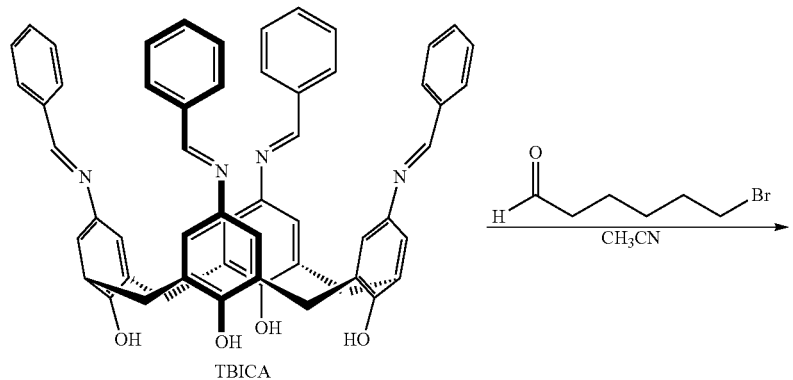

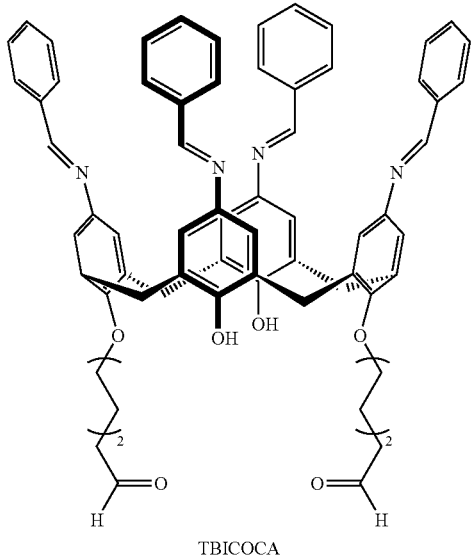
TBICOCA 500 mg of TBICA (0.6 mmol), anhydrous $K_2CO_3$ (830 mg, 6 mmol) and sodium iodide (810 mg, 5.4 mmol) are put into a dried round-bottom flask, and 150 ml of acetonitrile is added, then they are mixed under nitrogen exchange. After 10 minutes, 6-bromohexanal (644 mg, 3.6 mmol) is added, and the temperature of the reaction vessel is raised to 80° C. Then, the mixture is stirred for 24 hours. After the reaction, acetonitrile is decompressed and removed, and 150 ml of $CH_2Cl_2$ is used to dissolve the reaction product. Since KBr, KI, $K_2CO_3$, etc. obtained during the reaction do not dissolve, they are removed by being decompressed and filtered. The filtered solution is decompressed to remove the solvent and then completely dissolved in 5 ml of ethyl acetate. Then, if 40 ml of n-hexane is added, 5,11,17,23-tetrabenzyliminealkoxy-calix[4]arene (TBICOCA) is extracted as a yellow solid. This is recrystallized with $CHCl_3$/n-hexane to obtain a light-yellow solid product, TBICOCA (570 mg, yield 90%). Said reaction is represented by reaction 3.

$^1$H NMR (300 MHz, $CDCl_3$): δ 9.81(t, 2H, CHO), 8.46(s, 2H, N═CH), 8.24(s, 2H, N═CH), 7.86-7.82(m, 4H, Ar), 7.73-7.70(m, 4H, Ar), 7.43-7.31(m, 12H, Ar), 7.07(s, 4H, Ar), 6.83(s, 4H, Ar), 4.33(d, 4H, $ArCH_2Ar$, J=13 Hz), 4.04(t, 4H, $OCH_2$), 3.46(d, 4H, $ArCH_2Ar$, J=13 Hz), 2.57(t, 4H, $CH_2CHO$), 2.10 (t, 4H, $OCH_2CH_2$), 1.88-1.70(m, 8H, $CH_2CH_2$)

$^{13}$C NMR (300 MHz, $CDCl_3$): δ 202.07, 197.11, 159.61, 158.90, 148.21, 147.19, 145.93, 143.10, t136.07, 130.59-129.57, 128.83-128.08, 122.10, 121.54, 43.84, 31.73, 25.57

EXAMPLE 4
Preparation of 5,11,17,23-tetrabenzylimine-bromobutoxy-calix[4]-arene

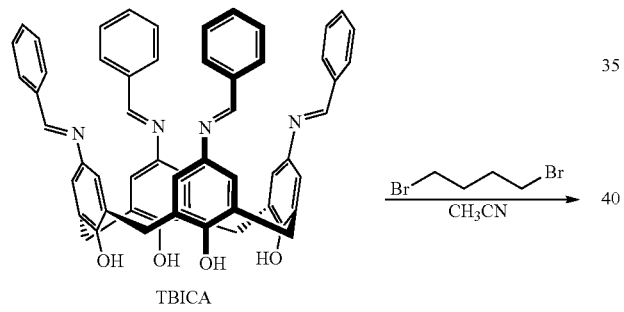

TBICA (500 mg, 0.6 mmol), anhydrous $K_2CO_3$ (830 mg, 6 mmol) and sodium iodide (1.08 g, 7.2 mmol) are put into a dried round-bottom flask, and 150 ml of acetonitrile is added, then they are mixed for 10 minutes at room temperature. 1,4-dibromobutane (1.3 g, 0.72 ml, 6 mmol) is added to the reaction vessel and the temperature of the reaction vessel is raised to 80° C. Then, the mixture is reacted for 24 hours. After the reaction vessel is cooled to room temperature, the solvent is decompressed and removed, and the remaining product is dissolved with 150 ml of $CH_2Cl_2$. Since KBr, KI, $K_2CO_3$, etc. obtained during the reaction do not dissolve, they are removed by being decompressed and filtered, and the filtered solution is decompressed to remove the solvent. After being extracted with ethyl acetate/n-hexane, it is decompressed and filtered to obtain a yellow solid product, 5,11,17,23-tetrabenzylimine-bromobutoxy-calix[4]arene (TBBCA). This solid is recrystallized with $CHCl_3$/n-hexane to obtain a light-yellow TBBCA (480 mg, 72%). Said reaction is represented by reaction 4.

$^1$H NMR (300 MHz, $CDCl_3$): δ 8.47(s, 2H, N═CH), 8.24 (s, 2H, N═CH), 7.98(s, 2H, ArOH), 7.86-7.83(dd, 4H, ArH), 7.73-7.70(dd, 4H, ArH), 7.41-7.31(m, 12H, ArH), 7.08(s, 4H, Ar), 6.83(s, 4H, Ar), 4.33(d, 4H, $ArCH_2Ar$, J=13 Hz), 4.06(t, 4H, $OCH_2$), 3.49(s, 4H, $ArCH_2Ar$, J=13 Hz), 3.45(t, 4H, $CH_2Br$), 2.37-2.29(m, $OCH_2CH_2$) 2.24-2.18(m, $CH_2CH_2Br$)

EXAMPLE 5
Preparation of 5,11,17,23-tetrabenzyliminemercapto-butoxycalix[4]-arene

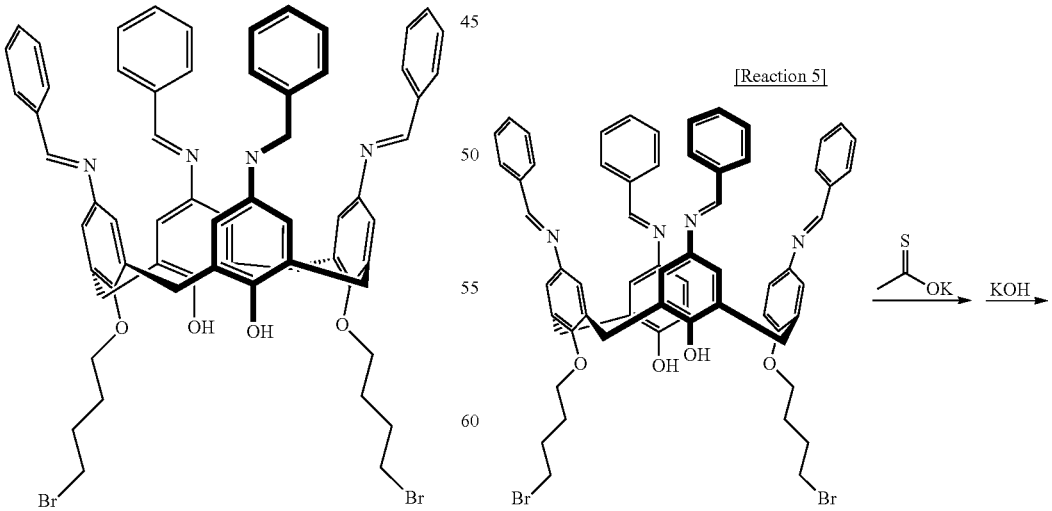

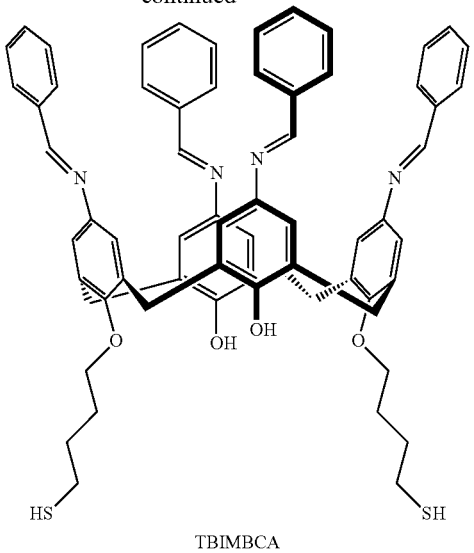

TBIMBCA

TBBCA (500 mg, 0.45 mmol) and potassium thioacetate (114.21 mg, 1 mmol) are put into a dried round-bottom flask, and dissolved in 60 ml of acetone, and sonic reacted for 90 minutes at room temperature under nitrogen exchange. After the reaction, the solvent is removed under decompressed pressure, and dissolved with 30 ml of $CH_2Cl_2$. Then, the precipitate that is not dissolved is decompressed and filtered, and then the filtered solution is washed with water twice and the organic layer is separated and dried with $MgSO_4$. The solid obtained by depressing and filtering the organic layer and then decompressing and drying the filtered solution is recrystallized using ethyl acetate/n-hexane, and decompressed and filtered to obtain a light-yellow solid crystal. The thus-obtained solid crystal is put in the round-bottom flask, and dissolved in a mixed solution in a ratio of $CH_2Cl_2$:methanol=5:1, and sonic reacted at room temperature under nitrogen exchange. After 1 minute, 1.0 M KOH (1 ml, 1 mmol) is added, and it is sonic reacted for 30 minutes. After the reaction, the solvent is removed under reduced pressure, and then it is dissolved in 5 ml of $CH_2Cl_2$ and washed with 0.1 M HCl solution once. After the organic layer is separated and dried with $MgSO_4$, it is decompressed and filtered, and the solvent of the filtered solution is removed under decompressed pressure to obtain a light-yellow 5,11,17,23-tetrabenzylimine-mercaptobutoxycalix[4]arene (TBIMBCA). The thus-obtained TBIMBCA is recrystallized with ethyl acetate/n-hexane to obtain a white solid crystal, TBIMBCA (450 mg, yield 73%). Said reaction is represented by reaction 5.

$^1$H NMR (300 MHz, $CDCl_3$): δ 8.48(s, 2H, N=CH), 8.17 (s, 2H, N=CH), 7.84(m, 4H, ArOH), 7.68(m, 4H, ArOR), 7.38(m, 6H, ArH), 7.28(m, 6H, ArOR), 7.10(s, 4H, ArH), 6.81(s, 4H, ArH), 4.34(d, 4H, $ArCHA_2r$), 4.04(t, 4H, $ArOCH_2$), 3.47(d, 4H, $ArCH_2Ar$, J=13 Hz), 3.03(t, 4H, $SHCH_2$), 2.38(m, 4H, $ArOCH_2CH_2$), 2.11(m, 4H, $CH_2CH_2$)

EXAMPLE 6

Preparation of Iminecalixarene Derivative Monolayer

A solution wherein TBICOCA synthesized in example 3 is dissolved in an organic solvent such as $CHCl_3$, etc. in a concentration of 0.1~5 mM is prepared. As shown in FIG. 1, a slide glass (amine chip) wherein an amine functional group is attached is put in the prepared solution for 1~24 hours, and then taken out and washed with chloroform, acetone and water, and dried to prepare the iminecalixarene monolayer of the present invention. Other iminecalixarene derivative monolayers are prepared according to the same method.

EXAMPLE 7

Preparation of Iminecalixarene Derivative Monolayer on a Gold Substrate

A solution wherein TBIMBCA synthesized in example 5 is dissolved in an organic solvent such as $CHCl_3$, etc. in a concentration of 0.1-5 mM is prepared. As shown in FIG. 2, a gold substrate is put in the prepared solution for 1~24 hours, and then taken out and washed with chloroform, acetone and water, and dried to prepare the iminecalixarene monolayer of the present invention. Other iminecalixarene derivative monolayers are prepared according to the same method. Said gold substrate can be used in various forms, but in general, a substrate vacuum plated with gold in a thickness of 100-300 nm after vacuum plating with chromium (Cr) or titanium (Ti), etc., glass, fused silica, silicon wafer, plastic, etc. in a thickness of 5-20 nm is preferable. The thus-prepared gold substrate is put in a piranha solution (a mixed solution in the ratio of strong sulfuric acid:30% hydrogen peroxide=3:1) for 10 seconds~1 minute just before use, and then washed with water and dried under nitrogen exchange, and used immediately. The formation of the monolayer is analyzed using infrared external reflection spectroscopy (FTIR-ERS).

EXAMPLE 8

Fixing Method of Oligo-DNA by Multi-Molecular Recognition

In the oligo-DNA fixation shown in FIG. 3, the microarray device of Genetics (United Kingdom) and the microarray device of Proteogen Co. (Korea) are used. An oligo-DNA having 9 consecutive guanine bases is dissolved in a BMT spotting solution in 6.75 pmol/μl to prepare a fixation solution. Using an array pin, said fixation solution coats the iminecalixarene derivative monolayer glass substrate (glass slide) as presented in FIG. 1 and prepared in the same method as that of example 6 in an amount of 1-5 nL, to fix oligo-DNA within a spot having a diameter of 150-180 μm. After 1-4 hours, the glass slide is washed in 500 ml of a BMT Wa-A-1 solution once for 1 minute, and washed twice with a BMT Wa-A-2 solution and then dried. In order to block the other positions where oligo-DNA is fixed, the washed glass slide is put in a BMT blocking solution of 250 ml and treated for 30 minutes. Then, it is washed with 500 ml of a BMT Wa-A-1 solution again once for 3 minutes, and washed twice with a BMT Wa-A-2 solution. Then, water is removed from it to dry.

EXAMPLE 9

Method for Irreversibly Fixing Only Oligo-DNA Having 9 Consecutive Guanine Bases by Multi-Molecular Recognition In the oligo-DNA fixation shown in FIG. 4, the microarray device of Genetics (United Kingdom) is used. In order to confirm the fixation efficiency of 6 different functional groups for fixation such as 9A, 9G, 9C, 9T, no, biotin, etc. of Table 1 below, each oligo-DNA in a BMT spotting solution in 6.75 pmol/μl is dissolved to prepare a fixation solution. Using an array pin, said fixation solution coats the iminecalixarene derivative monolayer glass substrate (glass slide) as presented in FIG. 1 and prepared in the same method as that of example 6 in an amount of 1-5 nL, to fix oligo-DNA within a spot having a diameter of 150-180 μm. After 1-4 hours, the glass slide is washed with 500 ml of a BMT Wa-A-1 solution once for 1 minute, and washed twice with a BMT Wa-A-2 solution and dried. In order to block the other positions where oligo-DNA is fixed, the washed glass slide is put in 250 ml of a BMT blocking solution and treated for 30 minutes. Then, it is washed with 500 ml of a BMT Wa-A-1 solution again once for 3 minutes, and washed twice with a BMT Wa-A-2 solution. After water is removed to dry, the oligo-DNA chip shown in FIG. 4 is prepared. Then, a chamber for hybridization having a diameter of 0.8 cm is firmly attached.

In order for the hybridization with the following fluorescent attached target DNA, a mixed solution of 2 μl of target DNA wherein a fluorescence of 2 pmol/μl is attached and 58 μl of BMT hyb-mixA is prepared in a 1.5 ml tube. After the mixed solution is heated in water of 100° C. for 3 minutes, and left on ice for 3 minutes so that it is cooled, 60 μl of the mixed solution is inserted in a glass slide wherein a chamber for hybridization is attached. Then, the glass slide is hybridized for 30 minutes at 50° C. in a constant temperature oven wherein the humidity is maintained. The glass slide that has gone through the hybridization is washed with a BMT Wa-B-1 (4×SSC, 0.1% SDS) solution for 2 minutes in a thermostat at 30° C., and with a BMT Wa-B-2 (4×SSC) solution for 2 minutes twice at room temperature. After it is dried, the fluorescent sensitivity is quantitatively analyzed using a microarray scanner (GSI Lumonics, U.S.A.). The actual results are as shown in FIG. 5. Said results show that oligo-DNA having 9 guanine bases went through fixation in high density, and the other bases did not affect the fixation.

EXAMPLE 10

Method for Comparing the Efficiency when Oligo-DNA Having 1-15 Consecutive Guanine Bases is Irreversibly Fixed by Multi-Molecular Recognition In the oligo-DNA fixation shown in FIG. 6, the microarray device of Genetics (United Kingdom) is used. In order to confirm the fixation efficiency of 6 different functional groups for fixation such as 1G, 4G, 7G, 9G, 12G (SEQ ID NO: 32), 15G (SEQ ID NO: 33), etc. of Table 2 below, each oligo-DNA in a BMT spotting solution in 6.75 pmol/□ is dissolved to prepare a fixation solution. Using an array pin, said fixation solution coats the iminecalixarene derivative monolayer glass substrate (glass slide) as presented in FIG. 1 and prepared in the same method as that of example 6 in an amount of 1-5 nL, to fix oligo-DNA within a spot having a diameter of 150-180 0. After 1-4 hours, the glass slide is washed with 500 □ of a BMT Wa-A-1 solution once for 1 minute, and washed twice with a BMT Wa-A-2 solution and dried. In order to block the other positions where oligo-DNA is fixed, the washed glass slide is put in 250 □ of a BMT blocking solution and treated for 30 minutes. Then, it is washed with 500 ml of a BMT Wa-A-1 solution again once for 3 minutes, and washed twice with a BMT Wa-A-2 solution. After being dried, the oligo-DNA chip shown in FIG. 4 is prepared. Then, a chamber for hybridization having a diameter of 0.8 cm is firmly attached.

TABLE 1

| | Sequence | Remarks |
|---|---|---|
| 9G | 5'-GGG GGG GGG AAA TCA ACC CAC AGC TGC A-3' (SEQ ID NO. 1) | probe |
| 9T | 5'-TTT TTT TTT TAA TCA ACC CAC AGC TGC A-3' (SEQ ID NO. 3) | |
| 9A | 5'-AAA AAA AAA TAA TCA ACC CAC AGC TGC A-3' (SEQ ID NO. 4) | |
| 9C | 5'-CCC CCC CCC CAA TCA ACC CAC AGC TGC A-3' (SEQ ID NO. 5) | |
| biotin | 5'-biotin-T ATA TAA TCA ACC CAC AGC TGC A-3' (SEQ ID NO. 6) | |
| no | 5'-AA TCA ACC CAC AGC TGC A-3' (SEQ ID NO. 7) | |
| c-DNA | 5'-Cy3-GT GCA GCT GTG GGT TGA TT-3' (SEQ ID NO. 2) | target |

TABLE 2

| | Sequence | Remarks |
|---|---|---|
| 1G | 5'-GAA TCA ACC CAC AGC TGC A-3' (SEQ ID NO. 8) | probe |
| 4G | 5'-GGG GAA TCA ACC CAC AGC TGC A-3' (SEQ ID NO. 9) | |
| 7G | 5'-GGG GGG GAA TCA ACC CAC AGC TGC A-3' (SEQ ID NO. 10) | |

TABLE 2-continued

| | Sequence | Remarks |
|---|---|---|
| 9G | 5'-GGG GGG GGG AAA TCA ACC CAC AGC TGC A-3' (SEQ ID NO. 1) | |
| 12G (SEQ ID NO: 32) | 5'-GGG GGG GGG GGG GAA TCA ACC CAC AGC TGC A-3' (SEQ ID NO. 11) | |
| 15G (SEQ ID NO: 33) | 5'-GGG GGG GGG GGG GGG GAA TCA ACC CAC AGC TGC A-3' (SEQ ID NO. 12) | |

In order for the hybridization with the fluorescent attached DNA which is the same as that used in example 9, a mixed solution of 2 μl of target DNA, wherein a fluorescence of 2 pmol/μl is attached, and 58 μl of BMT hyb-mixA is prepared in a 1.5 ml tube. After the mixed solution is heated in water of 100° C. for 3 minutes, and left on ice for 3 minutes so that it is cooled, 60 μl of the mixed solution is inserted in a glass slide wherein a chamber for hybridization is attached. Then, the glass slide is hybridized for 30 minutes at 50° C. in a constant temperature oven wherein the humidity is maintained. The glass slide that has gone through the hybridization is washed with a BMT Wa-B-1 (4×SSC, 0.1% SDS) solution for 2 minutes in a thermostat at 30° C., and with a BMT Wa-B-2 (4×SSC) solution for 2 minutes twice at room temperature. After it is dried, the fluorescent sensitivity is quantitatively analyzed using a microarray scanner (GSI Lumonics, U.S.A.). The actual results are as shown in FIG. 6. Said results show that in order for fixation, at least 7 consecutive guanine bases is required. In addition, they show that it presents the highest fixation density when there are 9 consecutive guanine bases.

EXAMPLE 11

Verification of the Fixation of Oligo-DNA by Multi-Molecular Recognition Through a Competitive Reaction with Imidazole In the oligo-DNA fixation shown in FIG. 7, the microarray device of Genetics (United Kingdom) is used. An oligo-DNA having a base sequence of 5'-GGG GGG GGG AAA TCA ACC CAC AGC TGC A-3' (SEQ ID NO. 1) is dissolved in a BMT spotting solution in 6.75 pmol/μl to prepare a fixation solution. Using an array pin, said fixation solution coats the iminecalixarene derivative monolayer glass substrate (glass slide) as presented in FIG. 1 and prepared in the same method as that of example 6 in an amount of 1-5 nL, to fix oligo-DNA within a spot having a diameter of 150-180 μm. However, imidazole of different concentrations is comprised in the concentration shown in FIG. 7 to coat the fixation solution. After 3 hours, the glass slide is washed with 500 ml of a BMT Wa-A-1 solution once for 1 minute, and washed twice with a BMT Wa-A-2 solution and dried. In order to block the other positions where oligo-DNA is fixed, the washed glass slide is put in 250 ml of a BMT blocking solution and treated for 30 minutes. Then, it is washed with 500 ml of a BMT Wa-A-1 solution again once for 3 minutes, and washed twice with a BMT Wa-A-2 solution. After water is removed from it to dry, the oligo-DNA chip shown in FIG. 4 is prepared. Then, a chamber for hybridization having a diameter of 0.8 cm is firmly attached.

In order for the hybridization with the fluorescent attached DNA which is the same as that used in example 9, a mixed solution of 2 μl of target DNA, wherein a fluorescence of 2 pmol/μl is attached, and 58 μl of BMT hyb-mixA is prepared in a 1.5 ml tube. After the mixed solution is heated in water of 100° C. for 3 minutes, and left on ice for 3 minutes so that it is cooled, 60 μl of the mixed solution is inserted in a glass slide wherein a chamber for hybridization is attached. Then, the glass slide is hybridized for 30 minutes at 50° C. in a constant temperature oven wherein the humidity is maintained. The glass slide that has gone through the hybridization is washed with a BMT Wa-B-1 (4×SSC, 0.1% SDS) solution for 2 minutes in a thermostat at 30° C., and with a BMT Wa-B-2 (4×SSC) solution for 2 minutes twice at room temperature. After it is dried, the fluorescent sensitivity is analyzed using a microarray scanner (GSI Lumonics, U.S.A.). The actual results are as shown in FIG. 7. Said results show that imidazole inhibits the fixation of consecutive guanines by multi-molecular recognition, and thus if at least 100 mM of imidazole is comprised, the fixation of oligo-DNA is hardly performed. That is, they show that as imidazole competes by molecular recognition, the fixation rate of the oligo-DNA having 9 consecutive guanine bases is lowered.

The composition of the solutions used for fixation, cleaning, etc. in examples 8-11 is as follows:

BMT spotting solution (4×SSC, 15% glycerol, 1× PBS)
BMT Wa-A-1 (2×SSC, 0.1% SDS)
BMT Wa-A-2 (0.1×SSC)
BMT blocking solution (milk casein 5% solution)
BMT hyb-mixA (4×SSC, 0.1% SDS, 50% glycerol, 1× PBS)
BMT Wa-B-1 (4×SSC, 0.1% SDS)
BMT Wa-B-2 (4×SSC)

EXAMPLE 12

Synthesis of 5,11,17,23-tetraminocalix[4]arene

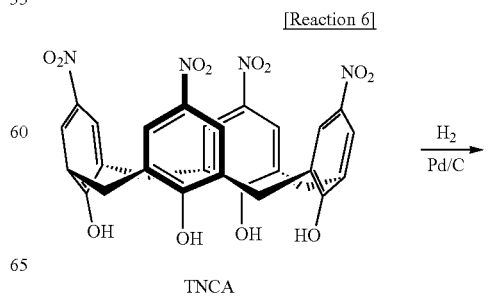

[Reaction 6]

TNCA

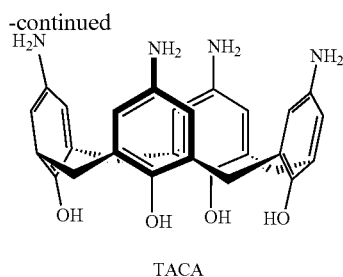

TACA 5,11,17,23-tetranitrocalix[4]arene (TNCA) is used as a starting material and synthesized according to the synthesis method presented in said reference material 3 to obtain a light-yellow solid product, 5,11,17,23-tetraminocalix[4]arene (TACA) in a yield of 75%.

EXAMPLE 13

Synthesis of 5,11,17,23-tetra(2,4-dimethyl)dibenzy-laminocalix[4]arene

[Reaction 7]

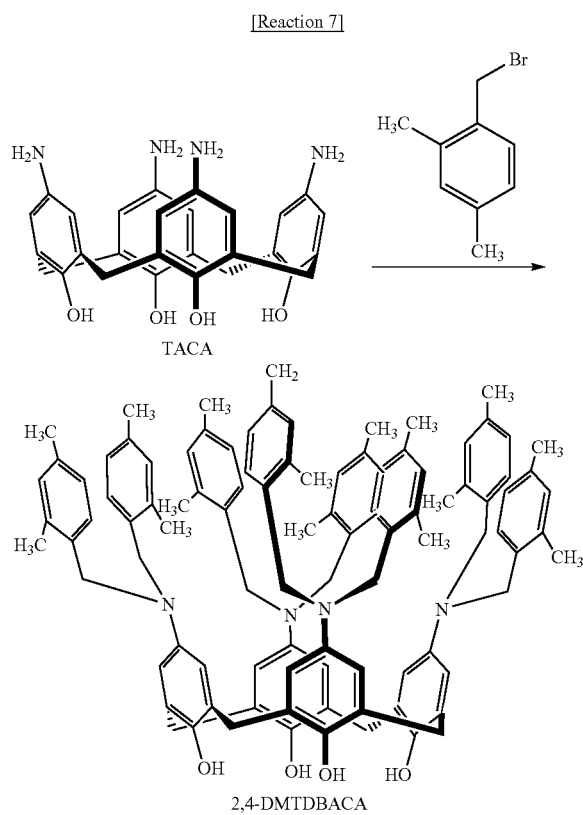

2,4-DMTDBACA

A magnetic bar, TACA (1.0 g, 2.05 mmol) and sodium iodide (3.0 g, 20.5 mmol) are put into a dried round-bottom flask, and the mixture is decompressed and dried. After it is dried and then 50 ml of anhydrous acetonitrile is added, they are mixed in a heater under nitrogen exchange. After 5 minutes, 2,4-dimethyl benzyl bromide (16.2 g, 82 mmol) is put in the reaction vessel, and then the temperature is raised and agitated. Then, pyridine (6.62 ml, 82 mmol) is added, and the mixture is reacted for 6 hours. After the reaction, the reaction vessel is cooled to room temperature, and the solvent is decompressed and removed. Then, after being dissolved in 150 ml of $CH_2Cl_2$, the organic layer is washed with water twice. After the organic layer is dried, it is filtered under reduced pressure, and the filtered solution is decompressed and removed. Then, it is recrystallized to $CH_2Cl_2$/MeOH to obtain 2.1 g of a light-gray solid product, 5,11,17,23-tetra(2,4-dimethyl)dibenzylaminocalix[4]arene (2,4-DMTDBACA) (yield 80%).

$^1$H NMR (300 MHz, CDCl$_3$); δ 10.14(s, 4H, ArOH), 7.28 7.12(m, 24H, ArH), 6.03(s, 8H, ArH), 4.24(s, 16H, ArNCH$_2$), 4.11(d, 4H, ArCH$_2$Ar, 13 Hz), 3.10(d, 4H, ArCH$_2$Ar, 13 Hz), 2.43(s, 12H, ArCH$_3$), 2.28(s, 12H, ArCH$_3$)

EXAMPLE 14

Synthesis of 5,11,17,23-(2,4-dimethyl)benzylimine-calix[4]arene

[Reaction 8]

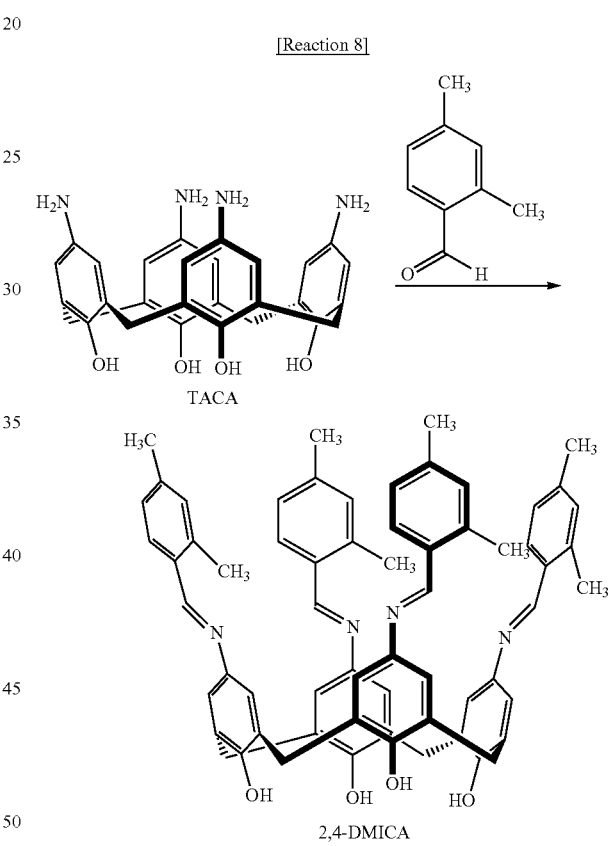

2,4-DMICA

TACA (100 mg, 0.2 mmol) and a magnetic bar are put into a dried round-bottom flask. 15 ml of acetonitrile is added to the reaction vessel and mixed. After 2,4-dimethylbenzaldehyde (322 mg, 2.4 mmol) is added, it is mixed for 2 hours under nitrogen exchange at room temperature. After the reaction, the mixture is decompressed and filtered, and the solvent is removed under reduced pressure. Then, the reactant is dissolved in a proper amount of $CH_2Cl_2$ and then 15 ml of n-hexane is added to obtain a light brown solid product. The product is dissolved in 3 ml of $CH_2Cl_2$ again, and then 15 ml of n-hexane is added to obtain 155 mg of a bright light brown solid product, 5,11,17,23-tetra(2,4-dimethyl)benzylimine-calix[4]arene (2,4-DMICA) (yield 81%).

$^1$H NMR (300 MHz, CDCl$_3$); δ 10.19(s, 4H, ArOH), 8.54 (s, 8H, N=CH), 7.79(d, 4H, ArH), 7.02(s, 4H, ArH), 7.01(d,

4H, ArH), 6.96(s, 8H, ArH), 4.30(d, 4H, ArCH$_2$Ar, 13 Hz), 3.61(s, 4H, ArCH$_2$Ar, 13 Hz), 2.43(s, 12H, ArCH$_3$), 2.30(s, 12H, ArCH$_3$)

EXAMPLE 15

Synthesis of 5,11,17,23-tetra(2,4-dimethyl)benzylaminocalix[4]arene

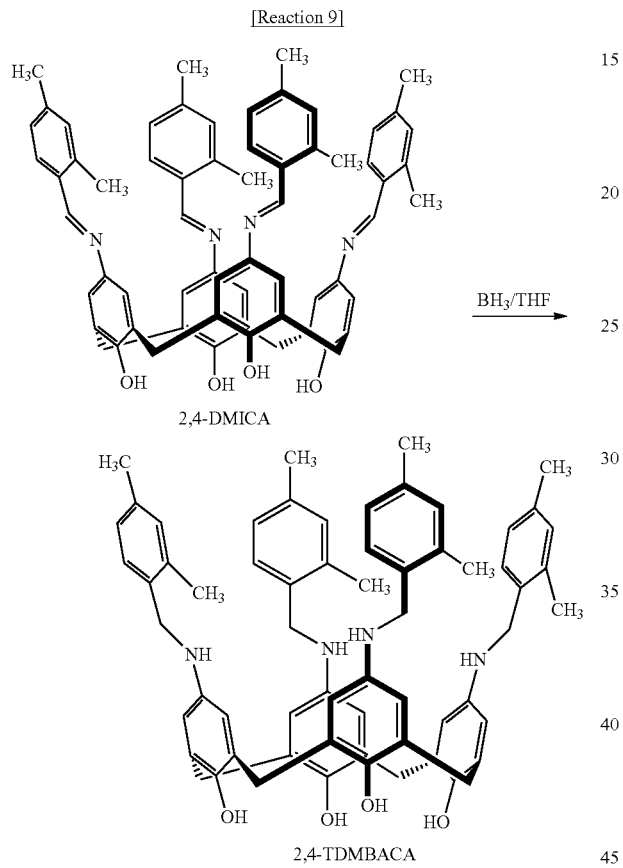

2,4-DMICA (100 mg, 0.1 mmol) and a magnetic bar are put into a dried round-bottom flask, and decompressed and dried. Then, 20 ml of anhydride THF is added and it is mixed under nitrogen exchange. After 10 minutes, BH$_3$/THF 1.0M solution (0.8 ml, 0.8 mmol) is added, and the mixture is reacted for 3 hours at room temperature. After the reaction, the solvent is removed under reduced pressure, and the product remaining in the flask is dissolved in CH$_2$Cl$_2$. Then, after being washed with a 0.1 M HCl solution twice, it is washed with distilled water twice. After the organic layer is separated and dried, it is decompressed and filtered to decompress and remove the filtered solution. Then, it is recrystallized to CH$_2$Cl$_2$/hexane to obtain 72 mg of a light yellow solid product, 5,11,17,23-tetra(2,4-dimethyl)benzylaminocalix[4]arene (2,4-TDMBACA) (yield 75%).

$^1$H NMR (300 MHz, CDCl$_3$); δ 9.86(s, 4H, ArOH), 7.33-7.18(m, 12H, ArH), 6.21(s, 8H, ArH), 4.21-4.09(m, 16H, ArCH$_2$Ar, ArNHCH$_2$), 3.58(s, 4H, NH), 3.22(d, 4H, ArCH$_2$Ar), 2.43(s, 12H, ArCH$_3$), 2.28(s, 12H, ArCH$_3$)

EXAMPLE 16

Synthesis of 5,11,17,23-tetra(2,4-dimethyletrabenzyl)benzylamino-calix[4]arene

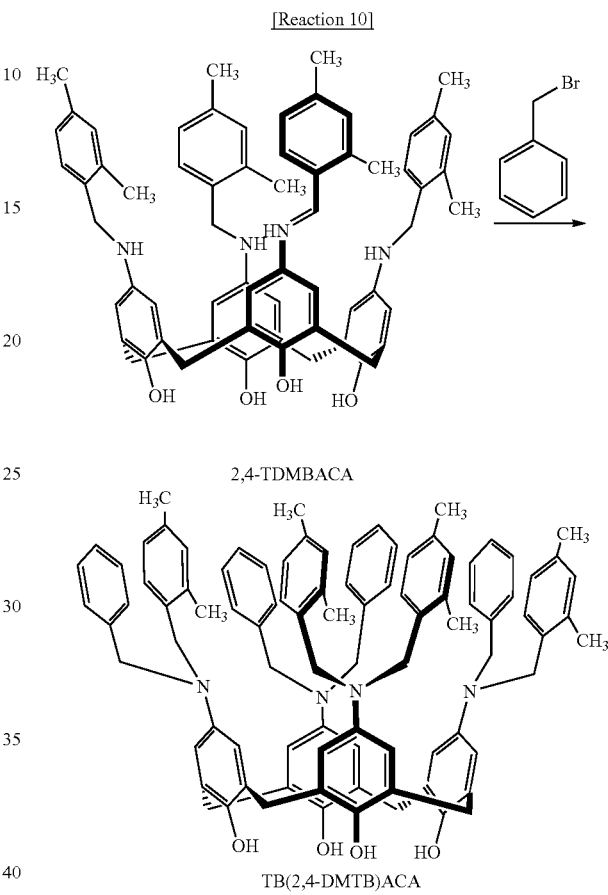

A magnetic bar and 2,4-TDMBACA (500 mg, 0.5 mmol) and sodium iodide (80 mg, 0.5 mmol) are put into a dried round-bottom flask, and decompressed and dried. After it is dried, 50 ml of anhydride acetonitrile is added, and then it is mixed in a heater under nitrogen exchange. After 5 minutes, benzylbromide (1.1 ml, 10 mmol) is added to the reaction vessel and exchange-mixed. Pyridine (0.8 ml, 10 mmol) is put in the reaction vessel, and reacted for 6 hours. After the reaction, the reaction vessel is cooled to room temperature, and then the solvent is decompressed and removed. Then, it is dissolved in 60 ml of CH$_2$Cl$_2$ and washed with water, and then the organic layer is dried and decompressed and filtered. Then, the filtered solution is decompressed and removed, and recrystallized to CH$_2$Cl$_2$/MeOH to obtain 521 mg of a light-gray solid product, 5,11,17,23-tetra(2,4-dimethyletrabenzyl)benzylamino-calix[4]arene (TB(2,4-DMTB)ACA) (yield 79%).

$^1$H NMR (300 MHz, CDCl$_3$) δ 10.01(s, 4H, ArOH), 7.35-7.10(m, 34H, ArH), 6.20-6.06(br, 8H, ArH), 4.31-4.01(m, 16H, ArCH$_2$Ar, ArNHCH$_2$), 3.14(d, 4H, ArCH$_2$Ar), 2.45(s, 12H, ArCH$_3$), 2.27(s, 12H, ArCH$_3$)

EXAMPLE 17

Synthesis of 5,11,17,23-tetra(2,4-dimethyl)dibenzylaminocalix[4]-arene-1,3-hexanal

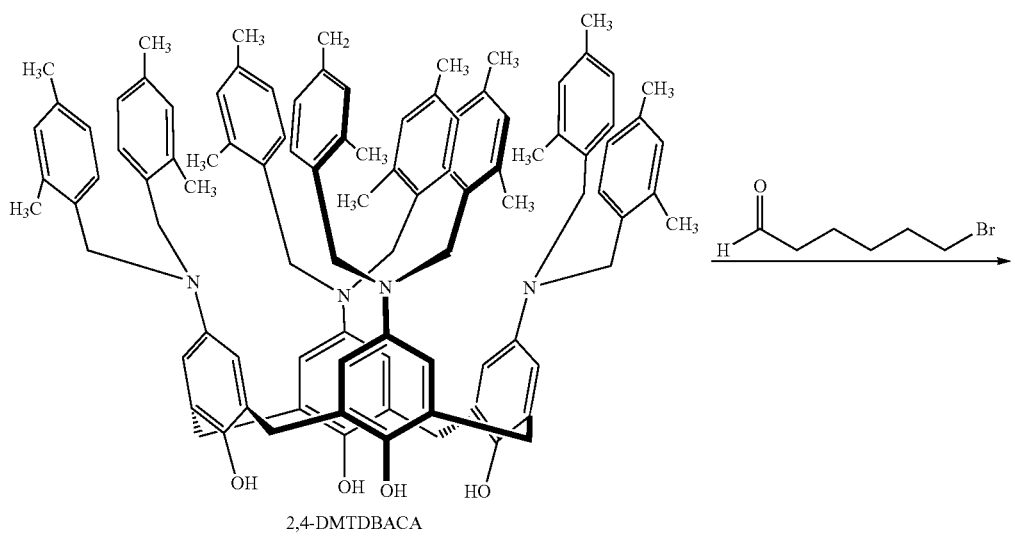

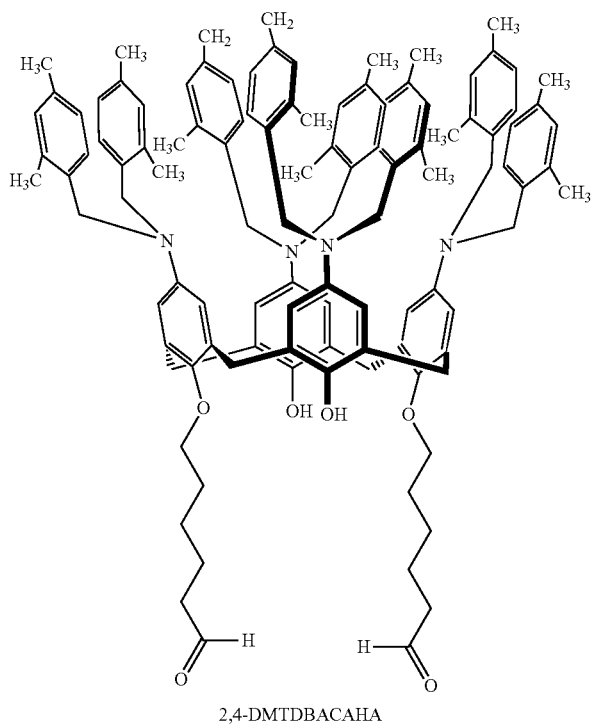

A magnetic bar and 2,4-DMTDBACA (500 mg, 0.35 mmol), $K_2CO_3$ (487 mg, 3.5 mmol), sodium iodide (473 mg, 3.15 mmol) are put in a dried round-bottom flask in order, and then 130 ml of anhydride acetonitrile is added to the reaction vessel under nitrogen exchange, and it is mixed in a heater. After adding 6-bromohexanal (376 mg, 2.1 mmol), it is exchange mixed for 16 hours. After the reaction, the reactant is cooled to room temperature, and the solvent is removed under reduced pressure. After dissolving the reactant with 130 ml of $CH_2Cl_2$, it is decompressed and filtered and the filtered solution is decompressed and removed. Then, it is recrystallized to $MeOH/CH_2Cl_2$ to obtain 432 mg of a light yellow solid product, 5,11,17,23-tetra(2,4-dimethyl)dibenzylaminocalix[4]-arene-1,3-hexanaldehyde(2,4-DMTDBACAHA) (yield 76%).

$^1$H NMR (300 MHz, $CDCl_3$); δ 9.78(s, 2H, CHO), 7.31 7.04(m, 12H, ArH), 6.11-6.02(br, 8H, ArH), 4.41-4.13(m, 20H, $ArNCH_2$, $ArCH_2Ar$), 3.89(t, 4H, $OCH_2$), 3.05(d, 4H, $ArCH_2Ar$, 13 Hz), 2.57-2.49(t, 4H, $CHOCH_2$), 2.45-2.39(m, 12H, $ArCH_3$), 2.31-2.25(m, 12H, $ArCH_3$), 2.12-1.98(t, $OCH_2CH_2$), 1.78-1.62(m, 8H, $CH_2CH_2$)

EXAMPLE 18

Synthesis of 5,11,17,23-tetra(2,4-dimethyltetrabenzyl)benzyl-aminobromobutoxycalix[4]arene

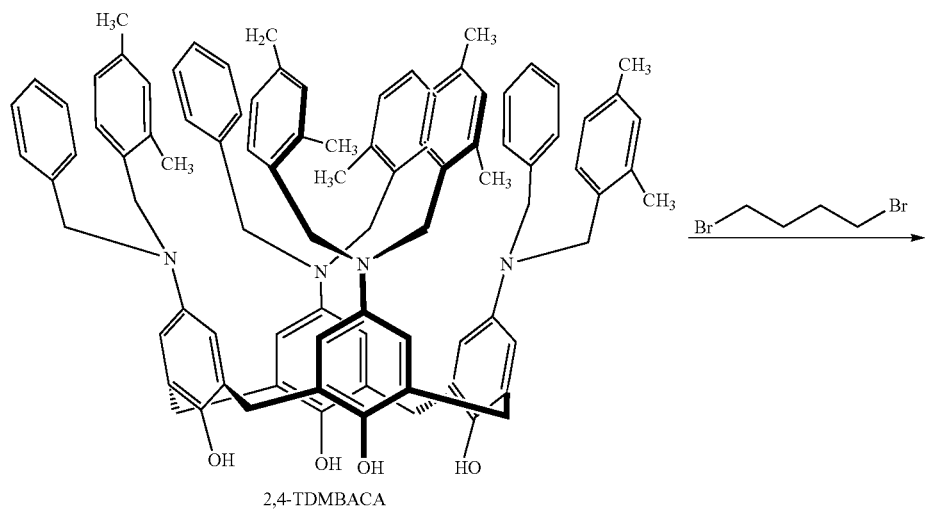

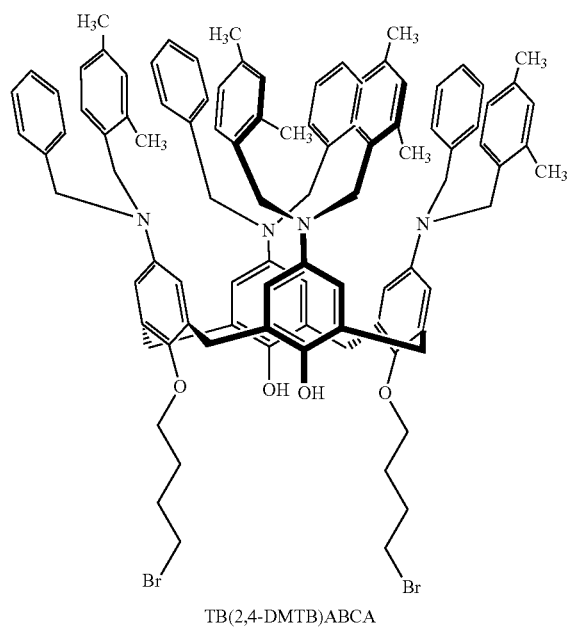

2,4-TDMBACA (500 mg, 0.5 mmol) and anhydride $K_2CO_3$ (619 mg, 5.0 mmol) and sodium iodide (674 mg, 4.5 mmol) are put into a dried round-bottom flask. 160 ml of anhydride acetonitrile is put into the reaction vessel and then it is mixed for 15 minutes at room temperature. 1,4-dibromobutane (1.03 g, 0.6 ml, 5.0 mmol) is added to the reaction vessel and it is exchange mixed for 20 hours. After the reaction vessel is cooled to room temperature, the solvent is decompressed and removed. Then, it is dissolved to $CH_2Cl_2$ and decompressed and filtered. The filtered solution is decompressed and removed, and recrystallized to EA/hexane. Then, it is decompressed and filtered to obtain 610 mg of a light brown solid product, 5,11,17,23-tetra(2,4-dimethyltetrabenzyl)benzylaminobromobutoxycalix[4]arene (TB(2,4-DMTB)ABCA) (yield 77%).

$^1$H NMR (300 MHz, $CDCl_3$); δ 7.81(s, 2H, ArOH), 7.29 7.04(m, 34H, ArH), 6.06-6.02(d, 8H, ArH), 4.38-4.11(m, 20H, ArNCH$_2$, ArCH$_2$Ar), 3.89(t, 4H, OCH$_2$), 3.04(d, 4H, ArCH$_2$Ar, 13 Hz), 2.46-2.43(m, 12H, ArCH$_3$), 2.41-2.40(m,

12H, ArCH$_3$) 2.31-2.27(t, 4H, BrCH$_2$), 2.16-2.06(m, 8H, CH$_2$CH$_2$)

EXAMPLE 19

Synthesis of 5,11,17,23-tetra(2,4-dimethyltetrabenzyl)benzyl-aminomercaptobutoxycalix[4]arene

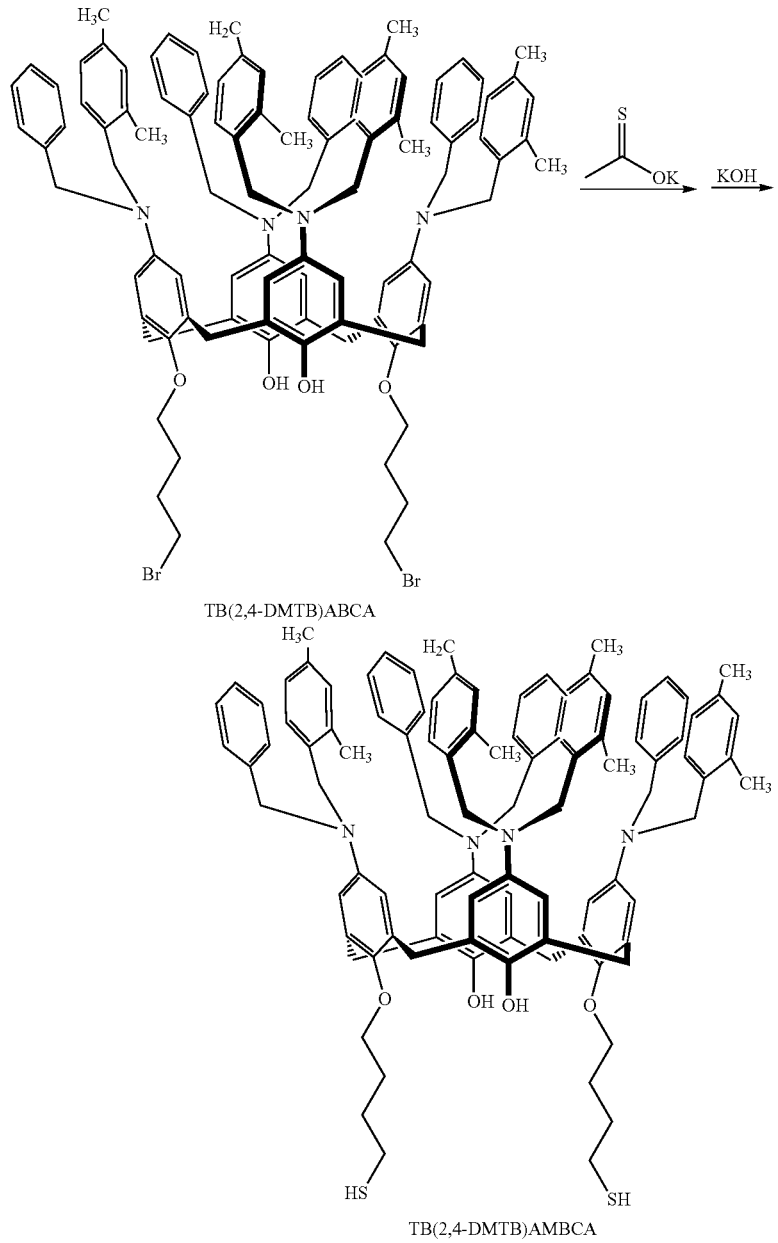

TB(2,4-DMTB)ABCA (500 mg, 0.31 mmol) and potassium thioacetate (212 mg, 1.86 mmol) are put into a dried round-bottom flask. Then, 60 ml of anhydride acetone is dissolved therein and it is sonic reacted at room temperature for 90 minutes under nitrogen exchange. After the reaction, the solvent is decompressed and removed, and then dissolved with 30 ml of CH$_2$Cl$_2$. After being decompressed and filtered, the filtered solution is washed with water twice and the organic layer is separated and dried. The solid obtained after decompressing and filtering the organic layer and decompressing and drying the filtered solution is recrystallized using EA/n-hexane and decompressed and filtered to obtain a light yellow solid crystal. The thus-obtained solid crystal is put in a round-bottom flask and dissolved in a mixed solution in a ratio of CH$_2$Cl$_2$:methanol=5:1 and sonic reacted at room temperature under nitrogen exchange. After 1 minute, 1.0 M KOH (1.5 ml, 1.5 mmol) is added and it is sonic reacted for 30 minutes. After the reaction, the solvent is decompressed and removed, and then dissolved in CH$_2$Cl$_2$ and washed with 0.1M HCl solution. After the organic layer is separated, it is dried and decompressed and filtered. The solvent of the filtered solution is removed under reduced pressure. After recrystallization using CH$_2$Cl$_2$/MeOH, 320 mg of a light yellow 5,11,17,23-tetra(2,4-methoxy)benzylaminomercaptobutoxycalix-[4]arene (TB(2,4-DMTB)AMBCA) (yield 73%) is obtained.

$^1$H NMR (300 MHz, CDCl$_3$); δ 7.84(s, 2H, ArOH), 7.29 7.01(m, 34H, ArH), 6.25-6.19(br, 8H, ArH), 4.36-4.11(m, 20H, ArNCH$_2$, ArCH$_2$Ar), 3.90(t, 4H, OCH$_2$), 3.05(d, 4H, ArCH$_2$Ar, 13 Hz), 2.30(t, 4H, SHCH$_2$), 2.45-2.39(m, 12H, ArCH$_3$), 2.31-2.25(m, 12H, ArCH$_3$) 2.05-2.02(m, CH$_2$CH$_2$)

EXAMPLE 20

Preparation of Aminocalixarene Derivative Monolayer as in FIG. 8

A solution, wherein 2,4-DMTDBACAHA synthesized in example 17 is dissolved in an organic solvent such as CHCl$_3$, etc. in a concentration of 0.1-5 mM, is prepared. As in FIG. 8, a slide glass (amine chip) wherein an amine functional group is attached is put in the prepared solution for 1~24 hours and taken out, it is washed with chloroform, acetone and water, respectively and dried. Then, the aminocalixarene derivative monolayer (A-type BMT oligo-DNA chip) of FIG. 8 is prepared. After the above-stated A-type is put in a BH$_3$-THF or NaBH$_4$ in MeOH reducing agent for 1~10 minutes, it is washed with water (DI water) for three times, and dried under nitrogen atmosphere to prepare the aminocalixarene derivative monolayer (B-type BMT oligo-DNA chip) of example 8.

EXAMPLE 21

Preparation of Aminocalixarene Derivative Monolayer on a Gold Substrate as in FIG. 9

A solution, wherein TB(2,4-DMTB)AMBCA synthesized in example 19 is dissolved in an organic solvent such as CHCl$_3$, etc. in a concentration of 0.1-5 mM, is prepared. As in FIG. 9, a gold substrate put in the prepared solution for 1~24 hours and taken out, it is washed with chloroform, acetone and water, respectively and dried. Then, the aminocalixarene derivative monolayer of FIG. 9 is prepared. Other aminocalixarene derivative monolayers are prepared according to the same method. Said gold substrate can be used in various forms, but in general, a substrate vacuum plated with gold in a thickness of 50-200 nm after vacuum plating with chromium (Cr) or titanium (Ti), etc. glass, fused silica, silicon wafer, plastic, etc. in a thickness of 2-10 nm is preferable. The thus-prepared gold substrate is put in a piranha solution (a mixed solution in the ratio of strong sulfuric acid:30% hydrogen peroxide=3:1) for 10 seconds~1 minute just before use, and then washed with water and dried under nitrogen exchange, and used immediately. The formation of the monolayer is analyzed using the infrared external reflection spectroscopy (FTIR-ERS).

Solution used in examples 22~25, oligo-DNA, oligo-DNA wherein fluorescence is attached, and C-DNA base sequence

TABLE 3

| Solution used in examples 22~25 | |
| --- | --- |
| BMT spotting solution 1 | 4xSSC, 15% glycerol, 1xPBS |
| BMT spotting solution 2 | 600 mM NH$_4$Cl, 15% glycerol, 1xPBS |
| BMT spotting solution 3 | 500 mM KCl, 15% glycerol, 1xPBS |
| BMT Wa-A-1 | 2xSSC, 0.1% SDS |
| BMT Wa-A-2 | 0.1xSSC |
| BMT blocking solution | milk casein 5% solution |
| BMT hyb-mix A | 4xSSC, 0.002% SDS, 50% glycerol, 1xPBS |
| BMT Wa-B-1 | 4xSSC, 0.1% SDS |
| BMT Wa-B-2 | 4xSSC |

TABLE 4

Optimum number of bases

| | Sequence | Remarks |
| --- | --- | --- |
| 1G | 5'-GAA TCA ACC CAC AGC TGC A-3' (SEQ ID NO. 13) | probe |
| 4G | 5'-GGG GAA TCA ACC CAC AGC TGC A-3' (SEQ ID NO. 14) | |
| 7G | 5'-GGG GGG GAA TCA ACC CAC AGC TGC A-3' (SEQ ID NO. 15) | |
| 9G | 5'-GGG GGG GGG AAA TCA ACC CAC AGC TGC A-3' (SEQ ID NO. 16) | |
| 12G (SEQ ID NO: 32) | 5'-GGG GGG GGG GGG AAA TCA ACC CAC AGC TGC A-3' (SEQ ID NO. 17) | |
| 15G (SEQ ID NO: 33) | 5'-GGG GGG GGG GGG GGG AAA TCA ACC CAC AGC TGC A-3' (SEQ ID NO. 18) | |
| Cy3-DNA | 5'-cy3-GT GCA GCT GTG GGT TGA TT-3' (SEQ ID NO. 19) | target |

TABLE 5

SNP for experiments

| | Sequence | Remarks |
|---|---|---|
| SNP-A | 5'-GGG GGG GGG TTT AC ATA GCA TAT CGA GGT GGG-3' (SEQ ID NO. 24) | probe |
| SNP-T | 5'-GGG GGG GGG TTT AC ATA GCA TTT CGA GGT GGG-3' (SEQ ID NO. 25) | |
| SNP-G | 5'-GGG GGG GGG TTT AC ATA GCA TGT CGA GGT GGG-3' (SEQ ID NO. 26) | |
| SNP-C | 5'-GGG GGG GGG TTT AC ATA GCA TCT CGA GGT GGG-3' (SEQ ID NO. 27) | |
| CN-A | 5'-A ATC AAC CCA CAG CTG AAA AAA CCC ACC TCG AAA TGC TAT GTG GAC-3' (SEQ ID NO. 28) | target for detecting |
| CN-T | 5'-A ATC AAC CCA CAG CTG AAA AAA CCC ACC TCG ATA TGC TAT GTG GAC-3' (SEQ ID NO. 29) | fluorescence |
| CN-G | 5'-A ATC AAC CCA CAG CTG AAA AAA CCC ACC TCG AGA TGC TAT GTG GAC-3' (SEQ ID NO. 30) | |
| CN-C | 5'-A ATC AAC CCA CAG CTG AAA AAA CCC ACC TCG ACA TGC TAT GTG GAC-3' (SEQ ID NO. 31) | |
| Cy3-DNA | 5'-cy3-GT GCA GCT GTG GGT TGA TT-3' (SEQ ID NO. 19) target | |

TABLE 6 for competitive reaction

| | Sequence | Remarks |
|---|---|---|
| 9A | 5'-AAA AAA AAA GAA TCA ACC CAC AGC TGC A-3' (SEQ ID NO. 20) | probe |
| 9T | 5'-TTT TTT TTT GAA TCA ACC CAC AGC TGC A-3' (SEQ ID NO. 21) | |
| 9C | 5'-CCC CCC CCC GAA TCA ACC CAC AGC TGC A-3' (SEQ ID NO. 22) | |
| 9G | 5'-GGG GGG GGG AAA TCA ACC CAC AGC TGC A-3' (SEQ ID NO. 16) | |
| 9G-1 | 5'-GGG GGG GGG AAA TCG CAC GTC TGT AGG-3' (SEQ ID NO. 23) | |
| Cy3-DNA | 5'-cy3-GT GCA GCT GTG GGT TGA TT-3' (SEQ ID NO. 19) target | |

TABLE 7

For experiments of maximum density

| | Sequence | Remarks |
|---|---|---|
| 9G | 5'-GGG GGG GGG AAA TCA ACC CAC AGC TGC A-3' (SEQ ID NO. 16) | probe |
| Cy3-DNA | 5'-cy3-GT GCA GCT GTG GGT TGA TT-3' (SEQ ID NO. 19) target | |

TABLE 8

Composition of the solution for competitive reaction (ul)

|  | 1:0 | 1:1 | 1:2 | 1:4 |
|---|---|---|---|---|
| 9G-1 (100 pmol/ul) | 1.5 | 1.5 | 1.5 | 1.5 |
| 9A, 9T, 9C, 9G, respectively | 0 | 1.5 | 3.0 | 6.0 |
| 2M NH₄Cl | 30 | 30 | 30 | 30 |
| 90% glycerol | 17 | 17 | 17 | 17 |
| distilled water | 51.5 | 50 | 48.5 | 45.5 |
| Total | 100 ul | 100 ul | 100 ul | 100 ul |

EXAMPLE 22

Determining the Optimum Number of Guanine Bases Irreversibly Fixed by Multi-Molecular Recognition on the Aminocalixarene Derivative Monolayer of FIG. 12

Fixation of Oligo-DNA on an Aminocalixarene Derivative Monolayer by Multi-Molecular Recognition The sample solution and concentration composition, etc. used for determining the number of guanine appropriate for multi-molecular recognition on an aminocalixarene derivative monolayer are as shown in Table 3. First, a mixed solution of 10ul of each of oligo-DNAs (100 pmol/ul) respectively having 1G, 4G, 7G, 9G, 12G (SEQ ID NO: 32), 15G (SEQ ID NO: 33) consecutive guanine bases of the following Table 4 and 148 ul of BMT spotting solution 3 is coated in an amount of 1-5 nl on the aminocalixarene derivative monolayer prepared for the fixation of oligo-DNA using a microarrayer (Genetix Qarray2) so as to fix it in size whose diameter is 150-180 um at the chamber for fixation for 1 hour, 2 hours, 4 hours, respectively at room temperature. After fixation, in order to remove the remaining oligo-DNA, the aminocalixarene derivative monolayer is washed with BMT Wa-A-1 (2×SSC, 0.1% SDS) at room temperature for 1 minute, and then washed with BMT Wa-A-2 (0.1×SSC), and blocked with a BMT blocking solution (milk casein 5% solution) at room temperature for 30 minutes. The treated aminocalixarene derivative monolayer is washed with BMT Wa-B-1 (4×SSC, 0.1% SDS) at room temperature for 3 minutes, and then washed and dried with a wash bottle of BMT Wa-A-2 (0.1×SSC).

Hybridization with the DNA (Cy3-DNA) Wherein Fluorescence is Attached

For a hybridization with the Cy3-DNA where fluorescence is attached, a chamber for hybridization is attached to the aminocalixarene derivative monolayer that has been dried after a fixation of oligo DNA. Then, 2 ul of the Cy3-DNA (5 nmol/ml) specified in Table 4 is mixed with 58 ul of BMT hyb-mixA (4×SSC, 0.002% SDS, 50% glycerol, 1× PBS) and heated in 100° C. water for 3 minutes. It is left on ice for 3 minutes, and coated with 60 ul using a micropipet, and then hybridized for 30 minutes to 50° C. in a constant temperature incubator maintaining humidity. After the hybridization, for the cleaning of aminocalixarene derivative monolayer, it is washed with BMT Wa-B-1 (4×SSC, 0.1% SDS) at 30° C. for 2 minutes. Then, it is washed with BMT Wa-B-2 (4×SSC) at room temperature for 2 minutes twice and dried to analyze the fluorescent sensitivity using a fluorescent scanner (GSI Lumonics, U.S.A.). The actual results are as in FIG. 12. Said results show that when oligo-DNA is fixed on an aminocalixarene derivative monolayer through multi-molecular recognition, at least 7 guanine bases are required and that it is fixed in the highest density when using 9 guanine bases.

EXAMPLE 23

Experiment Confirming the Differentiation of Single Nucleotide Polymorphism (SNP; Single Nucleotide Polymorphism) by Optimum Space Arrangement of FIG. 14 & FIG. 15

Confirmation of SNP on an Aminocalixarene Derivative Monolayer

The experiment for confirming the SNP on an aminocalixarene derivative monolayer prepared for the fixation of oligo-DNA is performed by first coating a mixed solution of 9.1 ul of oligo-DNAs (100 pmol/ul) of Table 6 that differ from each other only in one base at the same position and 35.9 ul of BMT spotting solution 1 in a thickness of 150-180 um in an amount of 1-5 nl using a micro array (Genetix Qarray2), and fixing it at a chamber for fixation for 3 hours at room temperature. After fixation, in order to remove the remaining oligo-DNA, the aminocalixarene derivative monolayer is washed with BMT Wa-A-1 (2×SSC, 0.1% SDS) at room temperature for 1 minute, and then washed with BMT Wa-A-2 (0.1×SSC) and blocked with BMT blocking solution (milk casein 5% solution) at room temperature for 30 minutes. The treated aminocalixarene derivative monolayer is washed with BMT Wa-B-1 (4×SSC, 0.1% SDS) at room temperature for 3 minutes, and then washed with a wash bottle of BMT Wa-A-2 (0.1×SSC) and dried.

Hybridization with C-DNA for Detecting DNA (Cy3-DNA) Wherein Fluorescence is Attached In order for hybridization, after a chamber for hybridization is attached to the monolayer, 2 ul of each of the C-DNA (5 nmol/ul) specified in Table 6 is mixed with 28 ul of BMT hyb-mixA (4×SSC, 0.002% SDS, 50% glycerol, 1× PBS) and heated in 100° C. water. It is left on ice for 3 minutes and cooled, then coated in an amount of 30 ul using a micropipet, and then hybridized for 30 minutes in a 55° C. constant temperature incubator. After the hybridization, for the cleaning of aminocalixarene derivative monolayer, it is washed with BMT Wa-B-1 (4×SSC, 0.1% SDS) at 30° C. for 2 minutes, and then washed with BMT Wa-B-2 (4×SSC) at room temperature for 2 minutes twice. Then, it is dried and the oligo-DNA monolayer capable of hybridization with DNA (Cy3-DNA) wherein fluorescence is attached is prepared.

Hybridization of C-DNA and Cy3-DNA Wherein Fluorescence is Attached

For the hybridization with Cy3-DNA wherein fluorescence is attached onto a monolayer that completed hybridization with C-DNA, first, the chamber for hybridization is attached, then 2 ul of Cy3-DNA (5 nmol/ml) of Table 6 is mixed with 28 ul of BMT hyb-mixA (4×SSC, 0.002% SDS, 50% glycerol, 1× PBS) and heated in 100° C. water for 3 minutes. Then, after being left on ice for 3 minutes and dried, it is coated in an amount of 30 ul using a micropipet, and then hybridized in a constant humidity incubator at 45° C. for 30 minutes. After the hybridization, for the cleaning of the aminocalixarene derivative monolayer, it is washed with BMT Wa-B-1 (4×SSC, 0.1% SDS) at 30° C. for 2 minutes, and washed twice with BMT Wa-B-2 (4×SSC) at room temperature for 2 minutes and dried. Then, using a fluorescent scanner (GSI Lumonics, U.S.A.), the SNP differentiation is confirmed by fluorescent sensitivity. The results are shown as FIGS. 14 & 15. The results show that other DNAs are not combined in hybridization at a position where an oligo-DNA having a difference of one base is fixed. Therefore, the results show that the technology according to the present invention can realize quick and precise SNP differentiation by optimum space arrangement between oligo-DNAs by being arranged securing a proper amount of space between the oligo-DNA being fixed.

EXAMPLE 24

Fixation Experiment of Highest Density in FIGS. 10 & 11

Oligo-DNA Fixation

The method for fixing oligo-DNA on an aminocalixarene derivative monolayer is performed by first coating a mixed solution of 9.1 ul of oligo-DNA (100 μmol/ul) of Table 7 and 35.9 ul of BMT spotting solution 1 on an aminocalixarene derivative monolayer prepared for the fixation of oligo-DNA in an amount of 1-5 nl using a micro array (Genetix Qarray2), and fixing it at a chamber for fixation for 3 hours at room temperature. After the fixation, for the removal of the remaining oligo-DNA, the aminocalixarene derivative monolayer is washed with BMT Wa-A-1 (2×SSC, 0.1% SDS) at room temperature for 1 minute, and then washed with BMT Wa-A-2 (0.1×SSC) and blocked with BMT blocking solution (milk casein 5% solution) at room temperature for 30 minutes. The treated aminocalixarene derivative monolayer is washed with BMT Wa-B-1 (4×SSC, 0.1% SDS) at room temperature for 3 minutes, and then washed with a wash bottle of BMT Wa-A-2 (0.1×SSC) and dried.

Hybridization with Cy3-DNA Wherein Fluorescence is Attached

For hybridization with Cy3-DNA wherein fluorescence is attached, first, the chamber for hybridization is attached, then 2 ul of Cy3-DNA (5 nmol/ml) of Table 7 is mixed with 28 ul of BMT hyb-mixA (4×SSC, 0.002% SDS, 50% glycerol, 1× PBS) and heated in 100° C. water and left on ice and cooled. Then, it is coated in an amount of 30 ul using a micropipet, and hybridized in an incubator at 50° C. for 30 minutes. After the hybridization, for the cleaning of the aminocalixarene derivative monolayer, it is washed with BMT Wa-B-1 (4×SSC, 0.1% SDS) at 30° C. for 2 minutes, and washed twice with BMT Wa-B-2 (4×SSC) at room temperature for 2 minutes and dried. Then, using a fluorescent scanner, the fluorescent sensitivity is confirmed to be compared and analyzed with the theoretical fluorescent sensitivity.

Drying an Amount of C-DNA Wherein Fluorescence is Attached on the Chip Substrate, Comparing and Analyzing it with the Theoretical Maximum Value After the Cy3-DNA wherein fluorescent of Table 7 is attached on an aminocalixarene derivative is coated with 1-5 nl, ½ of the theoretical maximum value (0.675 fmol/nl), using a microarray (Genetix Qarray2) and dried, it is analyzed using a fluorescent scanner. The results of comparing the theoretical fluorescent sensitivity and the experimental fluorescent sensitivity are shown in FIGS. 10 & 11, and the results of using Cy3-DNA where is attached fluorescence of about half the level of the theoretical maximum value appear to be the same as the results shown in the oligo-DNA fixed through hybridization. Therefore, the results show that an oligo-DNA close to the theoretical maximum value was fixed.

EXAMPLE 25

Confirmation Experiment on Irreversible Fixation of Only 9 Guanine Bases Using a Competitive Reaction with 9A, 9T, 9G, 9C-DNA of FIG. 16

Oligo-DNA for competitive reaction is prepared with a composition as shown in Table 7. At this time, different DNAs used in the competitive reaction are specified in Table 8 and their concentrations are prepared to be 0 time, 1 time, 2 times, and 4 times. Oligo-DNA is fixed by spotting each of the mixed solutions of oligo-DNAs, respectively prepared by the method shown in Table 7, on an aminocalixarene derivative monolayer in a thickness of 2 mm in an amount of 1 ul using a micropipet and fixing it at room temperature for 1 hour at a chamber for fixation. After the fixation, for the removal of the remaining oligo-DNA, the aminocalixarene derivative monolayer is washed with BMT Wa-A-1 (2×SSC, 0.1% SDS) at room temperature for 1 minute, and then washed with BMT Wa-A-2 (0.1×SSC) and blocked with BMT blocking solution (milk casein 5% solution) at room temperature for 30 minutes. The treated aminocalixarene derivative monolayer is washed with BMT Wa-B-1 (4×SSC, 0.1% SDS) at room temperature for 3 minutes, and then washed with a wash bottle of BMT Wa-A-2 (0.1×SSC) and dried.

Hybridization with Cy3-DNA Wherein Fluorescence is Attached

For a hybridization with Cy3-DNA wherein fluorescence is attached, first, a chamber for hybridization is attached, then 10 ul of Cy3-DNA (10 nmol/ml) of Table 8 is mixed with 590 ul of BMT hyb-mixA (4×SSC, 0.002% SDS, 50% glycerol, 1× PBS) and coated with 600 ul using a micropipet, and then hybridized at a 50° C. incubator for 30 minutes. After the hybridization, for the cleaning of the aminocalixarene derivative monolayer, it is washed with BMT Wa-B-1 (4×SSC, 0.1% SDS) at 30° C. for 2 minutes, and washed twice with BMT Wa-B-2 (4×SSC) at room temperature for 2 minutes and dried. Then, using a fluorescent scanner (GSI), the fluorescent sensitivity is confirmed. Said results are shown in FIG. 16. The results show that only 9 guanines are fixed by irreversible multi-molecular recognition and other bases do not largely affect the fixation regardless of whether they are consecutive or not. The results are actual experimental results showing the technology for preparing an oligo-DNA chip that can obtain replicable hybridization results wherein the bases that should be used in the hybridization do not participate in fixation and only consecutive specific base sequences participate in fixation so that the number of bases essential to the hybridization is always maintained.

Industrial Applicability

The present invention completely differs from the conventional fixing method of oligo-DNA following the method of chemical bonding or physical absorption, which is commonly used worldwide, and it is a novel method of irreversibly fixing oligo-DNA on a solid substrate by applying consecutive guanine bases by molecular recognition concept, i.e. multi-molecular recognition.

The present invention solves many problems occurring when fixing oligo-DNA on aldehyde-chip substrate through a chemical reaction between a high-priced oligo-DNA and aldehyde slide glass (aldehyde-chip substrate) in which the amine functional group, which is commonly used as a conventional chemical-binding method, is attached, in order to fix oligo-DNA on a solid substrate when preparing an oligo-DNA chip, so that anybody can easily prepare oligo-DNA chip.

Oligo-DNA chips prepared by using oligo-DNA where a high-priced functional group is attached has difficulty in obtaining a reproducibility in the step of fixation, and thus the period for the research and development is long, and this prevents many bio-businesses from moving from R & D to commercialization. In addition, when selecting oligo-DNA which brings the optimal hybridization results by testing hundreds of thousands of oligo-DNA base sequences, many abandon developing products due to the burden of the research and development expenses.

In the present invention, as shown in FIG. 3, since the consecutive guanine bases are fixed to iminecalixarene derivatives monolayer (BMT imine chip) by multi-molecular recognition, the density of oligo-DNA to be fixed under the same condition is always uniform, and thus it shows very high reproducibility. In addition, in FIG. 3, the space formed by fixing consecutive guanine base to the surface of substrate carries out hybridization by easily entering the space between oligo-DNA wherein c-DNA that should be combined with the surface of the substrate is fixed. Accordingly, there is an advantage over the conventional oligo-DNA chips in which the oligo-DNA is densely fixed, in that it can proceed with hybridization several or tens of times faster, thus allowing a faster diagnosis. Oligo-DNA which is fixed by molecular recognition is fixed according to a multi-molecular recognition to BMT imine chips in a solution, and thus it is possible for oligo-DNA to prepare the fixed oligo-DNA chip with high density even if the density of oligo-DNA used is used with the conventional level of $1/3$-$1/10$.

In addition, in the present invention, it takes approximately 2-4 hours to fix oligo-DNA, and then it is washed and dried. Thus, it makes it possible to bring simplicity and rapidity to the preparation of oligo-DNA chips.

Particularly, in FIGS. 4 & 6, oligo-DNA is irreversibly fixed on iminecalixarene derivatives self-assembly monolayer by multi-molecular recognition of nine consecutive guanine bases, and the fluorescent analysis results of hybridization shows that the fixation density of the fixed oligo-DNA is 5 to 30 times as high as that of the conventional method.

As such, the present invention can prepare oligo-DNA chips faster than the technology for preparing oligo-DNA chips by the conventional oligo-DNA fixation, and it reduces the costs of the research and development based on a high level of reproducibility. In addition, it is an epochal, novel technique that makes it possible to prepare products with a $1/3$-$1/5$ of the costs of the conventional method when preparing products. Accordingly, it can be applied to various DNA chip preparations later on based on the present invention.

In addition, as another aspect of the present invention, the present invention is a novel technology that can solve all problems that appear in the currently existing technologies for preparing a DNA chip: for example, according to the conventional technology, it is impossible to perform high speed hybridization; it is impossible to secure a technology for diagnosing single nucleotide polymorphism (SNP); it is difficult to obtain the reproducibility of DNA chips which appears because it is difficult to maintain hybridization results shown by performing a chemical bonding between amine functional groups present in three bases such as A, C, G and the aldehyde functional groups of aldehyde-chip substrates; and it is difficult to perform uniform density fixation, wherein oligo-DNA is fixed uniformly on a prepared chip.

The present invention provides an aminocalixarene derivative capable of irreversible molecular recognition of consecutive guanine groups, a technology for preparing oligo-DNA chip substrate prepared in the form of its self-assembled monolayer, an oligo-DNA chip prepared by irreversibly fixing an oligo-DNA by voluntary molecular recognition on the chip substrate surface and a technology for preparing the same. As shown in said examples and drawings, this fixation technology maintains the space between the bases automatically and appropriately as much as the space occupied when consecutive bases are irreversibly fixed on the bottom when the base is arranged while being fixed. This space is a space sufficient for c-DNA to freely enter the bottom of chip substrate during hybridization, and thus the time of hybridization can be proceeded with high speed. At the same time, the number of bases used for bonding bases when hybridizing can always be maintained in maximum; therefore, this is a novel technology wherein hybridization can be performed with such a high specificity as to allow the confirmation of the difference of a single base on an on-off basis.

Additionally, the present invention provides a fixed oligo-DNA monolayer to the maximum density level while maintaining the appropriate level of space wherein all kinds of oligo-DNA are fixed by attaching said compounds to the solid substrate such as a glass substrate (amine slide glass) having amine functional group or to the gold substrate (gold thin film or gold) without any treatment, that is, iminecalixarene derivatives provide a chip substrate for fixing oligo-DNA manufactured as a monolayer, that is, to manufacture an oligo-DNA chip. And then, the present invention provides a fundamental technology essential for making oligo-DNA chip with the same and reproductable products on all solid substrate.

Additionally, according to the present invention, oligo-DNA is fixed in an aqueous solution without permitting empty space by a novel technology, that is, multi-molecular recognition. Thus, a maximum number of oligo-DNAs are fixed, that is, the present invention is a novel technology that makes oligo-DNAs assemble voluntarily so that hybridization can be performed with high-speed while fixing oligo-DNA to the maximum density. Thus, the present invention provides a technology for manufacturing oligo-DNA chips with the highest level of sensitivity that can make a diagnosis by sensing c-DNA with a low concentration. At the same time, since an oligo-DNA is always fixed in maximum density, it provides a producing technology of oligo-DNA chip having a reproductivity which is essential in making it as a product. The conventionally-used chip substrate should be produced by using oligo-DNA where a high-priced reactor is attached, and it is very difficult to obtain the productivity at the stage of fixing oligo-DNA. Thus, the period for the research and development is very long, and moreover, it was a reason why the research and development could not move on to the product stage. By using the technology of the present invention of recognizing molecular, which makes it easy to manufacture, and by verifying hundreds-thousands of oligo-DNA base sequences, it can reduce the burden of the research and development when proceeding with oligo-DNA chip development and product by selecting oligo-DNA which brings the results of the maximum hybridization. In addition, the present invention provides a novel technology that make the optimal oligo-DNA chip release rapidly and timely by obtaining the productivity. If the fundamental technology for the production of chip provided in the present invention is used, the production and commercialization of various gene chips can be made rapidly.

In addition, the present invention can produce oligo-DNA chip with a high density by using oligo-DNAs for fixation by molecular recognition only 3 to 5 times the amount of oligo DNAs fixed on the surface. Thus, the present invention makes it possible to produce oligo-DNAs with only a $1/10$~$1/100$ of costs incurred for the production of the conventional oligo-DNA chip, thus saving enormous production costs.

Additionally, the present invention is completely different from the conventional method of fixing oligo-DNA by chemical bonding or physical absorption, which is commonly used worldwide, and it is a novel method of irreversibly fixing oligo-DNA to a solid substrate phase by applying consecutive guanine bases by molecular recognition definition, i.e. multi-molecular recognition.

The invention claimed is:

1. A self-assembled monolayer solid substrate comprising aminocalixarene as following Formula 5 or 6 and a solid substrate selected from the group consisting of glass, silicon-wafer, quartz, and gold, wherein the surface of the glass, silicon wafer, quartz, and gold is functionalized with amine or thiol, wherein the aminocalixarene derivatives are attached to the solid substrate through at least one of the thiol, the aldehyde, and the carboxyl groups of the aminocalixarene:

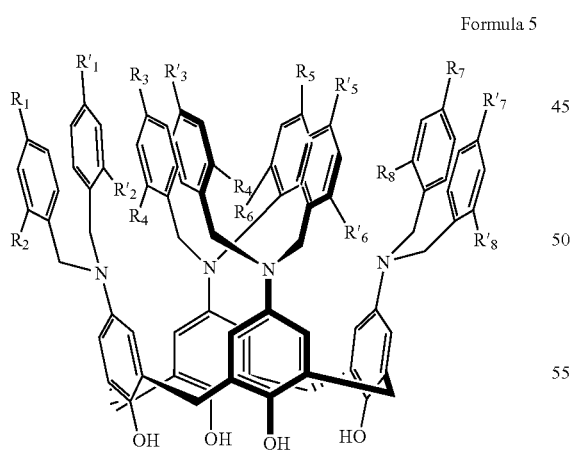

Formula 5 wherein, $R_1$, $R_2$, $R_3$, $R_4$, $R_5$, $R_6$, $R_7$, $R_8$, $R'_1$, $R'_2$, $R'_3$, $R'_4$, $R'_5$, $R'_6$, $R'_7$, $R'_8$ are independently selected from the group consisting of —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR, and in said —COOR, R represents —$CH_3$ or —$C_2H_5$; wherein $R_1=R_2=R_3=R_4=R_5=R_6=R_7=R_8$, and $R'_1=R'_2=R'_3=R'_4=R'_5=R'_6=R'_7=R'_8$, but $R_1 \neq R'_1$;

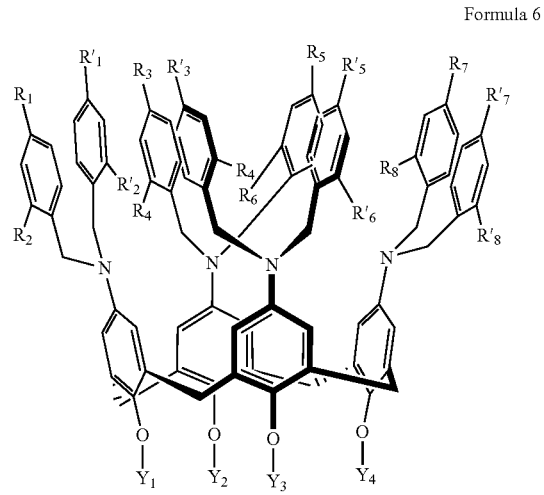

Formula 6 wherein, $R_1$, $R_2$, $R_3$, $R_4$, $R_5$, $R_6$, $R_7$, $R_8$, $R'_1$, $R'_2$, $R'_3$, $R'_4$, $R'_5$, $R'_6$, $R'_7$, $R'_8$ are independently selected from the group consisting of —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR, and in said —COOR, R represents —$CH_3$ or —$C_2H_5$;

$Y_1$, $Y_2$, $Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —(CH₂CH₂O)$_m$—CH₂CH₂—SH, —(CH₂)$_m$—C₆H₄(CH₂)$_c$—Z, and —CO—(CH₂)$_{m-1}$—C₆H₄—(CH₂)$_c$—Z;

n=2-15, m=1-10, c=0-10, Z=—SH, —CHO, —COOH, —NH₂, and —C₆H₄— and —C₆H₅ are phenyl group; wherein R₁=R₂=R₃=R₄=R₅=R₆=R₇=R₈, and R'₁=R'₂=R'₃=R'₄=R'₅=R'₆=R'₇=R'₈, but R₁≠R'₁.

2. An oligo-DNA chip comprising an oligo-DNA comprising at least 7 consecutive guanine bases and the self-assembled monolayer solid substrate of claim 1, wherein the guanine bases are attached to the aminocalixarene of the self-assembled monolayer solid substrate.

3. A self-assembled monolayer solid substrate comprising aminocalixarene as following formula 7 or 8 to a solid substrate selected from the group consisting of glass, siliconwafer, quartz, and gold, wherein the surface of the glass, silicon wafer, quartz, and gold is functionalized with amine or thiol, wherein the aminocalixarene are attached to the solid substrate through at leaset one of the thiol, the aldehyde, and the carboxyl groups of the aminocalixarene:

Formula 7

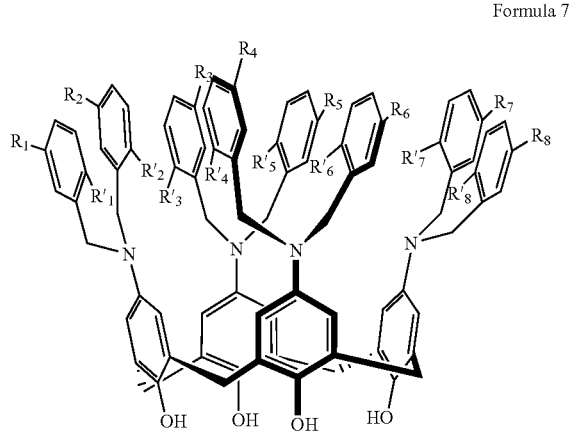

wherein, R₁, R₂, R₃, R₄, R₅, R₆, R₇, R₈, R'₁, R'₂, R'₃, R'₄, R'₅, R'₆, R'₇, R'₈ are independently selected from the group consisting of —CH₃, —C₂H₅, —C₃H₇, —OCH₃, —Cl, —C₆H₅, —OH, —OCH₂CH₃, —Br, —CF₃, —OCH₂C₆H₅, —OC₆H₅, —OC₆H₄CH₃, —OC₆H₄C(CH₃)₃, —OC₆H₄CF₃, —OC₆H₄Cl, —OCOCH₃, —NHCOCH₃, —CONHCH₃, —CN, COOH, and —COOR, and in said —COOR, R represents —CH₃ or —C₂H₅; wherein R₁=R₂=R₃=R₄=R₅=R₆=R₇=R₈, and R'₁=R'₂=R'₃=R'₄=R'₅=R'₆=R'₇=R'₈, but R₁≠R'₁;

Formula 8

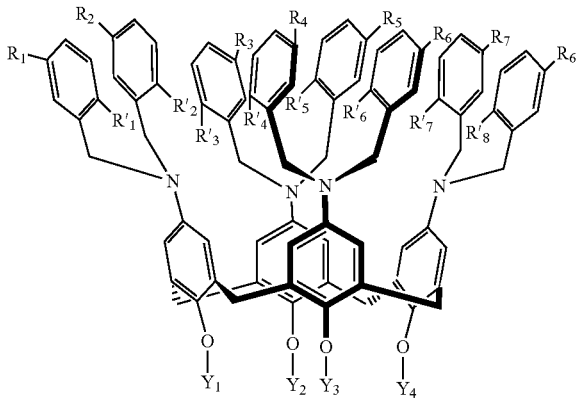

wherein R₁, R₂, R₃, R₄, R₅, R₆, R₇, R₈, R'₁, R'₂, R'₃, R'₄, R'₅, R'₆, R'₇, R'₈ are independently selected from the group consisting of —CH₃, —C₂H₅, —C₃H₇, —OCH₃, —Cl, —C₆H₅, —OH, —OCH₂CH₃, —Br, —CF₃, —OCH₂C₆H₅, —OC₆H₅, —OC₆H₄CH₃, —OC₆H₄C(CH₃)₃, —OC₆H₄CF₃, —OC₆H₄Cl, —OCOCH₃, —NHCOCH₃, —CONHCH₃, —CN, COOH, and —COOR, and in said —COOR, R represents —CH₃ or —C₂H₅;

Y₁, Y₂, Y₃ and Y₄ are independently selected from the group consisting of —H, —(CH₂)$_n$—CH=O, —(CH₂)$_n$—SH, —(CH₂CH₂O)$_m$—CH₂CH₂—CH=O, —(CH₂CH₂O)$_m$—CH₂CH₂—SH, —(CH₂)$_m$—C₆H₄—(CH₂)$_c$—Z, and —CO—(CH₂)$_{m-1}$—C₆H₄—(CH₂)$_c$—Z;

n=2-15, m=1-10, c=0-10, Z=—SH, —CHO, —COOH, —NH₂, and —C₆H₄— and C₆H₅ are phenyl group; wherein R₁=R₂=R₃=R₄=R₅=R₆=R₇=R₈, and R'₁=R'₂=R'₃=R'₄=R'₅=R'₆=R'₇=R'₈ but R₁≠R'₁.

4. An oligo-DNA chip comprising an oligo-DNA comprising at least 7 consecutive guanine bases and the self-assembled monolayer solid substrate of claim 3, wherein the guanine bases are attached to the aminocalixarene of the self-assembled monolayer solid substrate.

* * * * *

SEQUENCE LISTING

<160> NUMBER OF SEQ ID NOS: 33

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 gggggggggga aatcaaccca cagctgca                                        28

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgcagctgt gggttgatt                                                   19

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttttttt aatcaaccca cagctgca                                         28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaat aatcaaccca cagctgca                                         28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccccccccc aatcaaccca cagctgca                                         28

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
tatataatca acccacagct gca                                           23
```

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aatcaaccca cagctgca                                                 18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaatcaaccc acagctgca                                                19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggggaatcaa cccacagctg ca                                            22

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 ggggggggaat caacccacag ctgca                                        25

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggggggggg gggaatcaac ccacagctgc a                                  31

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggggggggg ggggggaatc aacccacagc tgca                               34
```

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaatcaaccc acagctgca                                                  19

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggggaatcaa cccacagctg ca                                              22

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggggggaat caacccacag ctgca                                           25

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gggggggggga aatcaaccca cagctgca                                       28

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggggggggg ggaaatcaac ccacagctgc a                                    31

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gggggggggg ggggaaatc aacccacagc tgca                                  34

<210> SEQ ID NO 19

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgcagctgt gggttgatt                                                   19

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaaaaaaag aatcaaccca cagctgca                                         28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttg aatcaaccca cagctgca                                         28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 ccccccccog aatcaaccca cagctgca                                         28

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gggggggga aatcgcacgt ctgtagg                                           27

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 ggggggggt ttacatagca tatcgaggtg gg                                     32

<210> SEQ ID NO 25
<211> LENGTH: 32
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 25
gggggggggt tacatagca tttcgaggtg gg                                    32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggggggggt tacatagca tgtcgaggtg gg                                    32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gggggggggt tacatagca tctcgaggtg gg                                    32

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aatcaaccca cagctgaaaa aacccacctc gaaatgctat gtggac                    46

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aatcaaccca cagctgaaaa aacccacctc gatatgctat gtggac                    46

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatcaaccca cagctgaaaa aacccacctc gagatgctat gtggac                    46

<210> SEQ ID NO 31
<211> LENGTH: 46
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 31
aatcaaccca cagctgaaaa aacccacctc gacatgctat gtggac                    46

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gggggggggg gg                                                         12

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gggggggggg ggggg                                                      15
```